Figure 1:
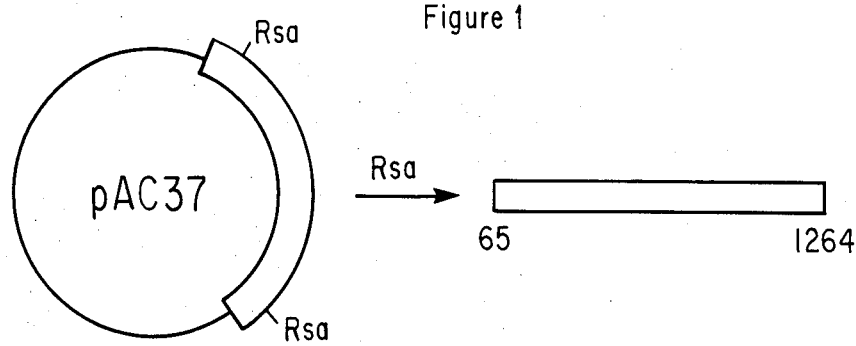
Figure 1:
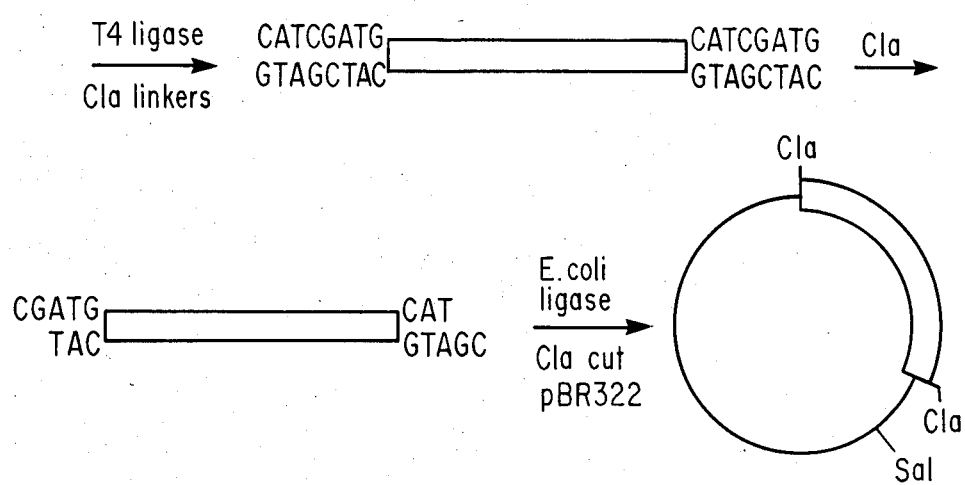
Figure 1:
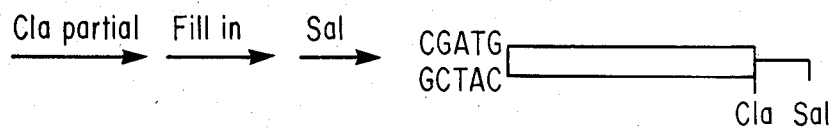
Figure 1:
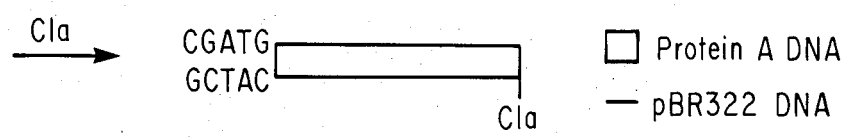

United States Patent [19]

Palmer et al.

[11] Patent Number: 4,691,009

[45] Date of Patent: Sep. 1, 1987

[54] HYBRID PROTEINS PRODUCED BY AN ULTRAHIGH PROKARYOTIC EXPRESSION SYSTEM

[75] Inventors: John L. Palmer; Algis Anilionis, both of Arlington, Mass.

[73] Assignee: Repligen Corporation, Cambridge, Mass.

[21] Appl. No.: 686,342

[22] Filed: Dec. 26, 1984

[51] Int. Cl.$^4$ .............................................. C07K 15/00
[52] U.S. Cl. ................................................... 530/350
[58] Field of Search ........................... 424/85; 530/350

[56] References Cited

U.S. PATENT DOCUMENTS 4,322,274  3/1982  Wilson et al. ......................... 424/85

OTHER PUBLICATIONS

Chem. Abstr., vol. 104, (1986) 63133.
Waldman, A. S. et al. (1983), "Purification and Characterization of Herpes Simp. Virus (Type 1), Thymidine Kinase . . . ", J. Bact., 258:11571-11575.
Derom, C. et al. (1982), "High-Level Synthesis in E. coli of the SV40 Small-t Antigen Under Control of . . . ", Gene, 17:45-54.
Yoakum, G. H. et al. (1982), "Amplication of the uvrA Gene Product of E. coli to 7% of Cellular Protein by Linkage to the . . . ", Proc. Natl. Acad. Sci., 79:1766-1770.
Oehmichen, R. et al. (1984), "Construction of an E. coli Strain Overproducing the Tn10-Encoded TET Repressor and Its Use . . . ", EMBO J., 3:539-543.
Bagdasarian, M. (1983), "Activity of the Hybrid Trp--Lac(tac) Promoter of E. coli in Pseudomonas putida . . . ", Gene, 26:273-282.
Bikel, I. et al. (1938), "Purification of Biologically Active Simian Virus 40 Small Tumor Antigen", Proc. Natl. Acad. Sci. U.S.A., 80:906-910.
Amann, E. et al. (1984), "Vectors Bearing a Hybrid Trp-Lac Promoter Useful for Regulated Expression of Cloned Genes in E. coli", Gene, 25:167-178.
Shineberg, B. and Zipser, D. (1973), "The lon Gene and Degradation of β-Galactosidase Nonsense Fragments", J. of Bact., 116:1469-1471.
Chung, C. H. and Goldberg, A. L. (1981), "The Product of the lon(capR) Gene in E. coli is the ATP-Dependent Protease . . . ", Proc. Natl. Acad. Sci., 78:4931-4935.
Sreedhara Swamy, K. H. and Goldberg, A. L. (1981), "E. coli Contains Eight Soluble Proteolytic Activities, One Being ATP Dependent", Nature, 292:652-654.
Mount, D. W. (1980), "The Genetics of Protein Degradation in Bacteria", Ann. Rev. Genet., 14:279-319.
Hautala, J. A. et al. (1979), "Increased Expression of a Eukaryotic Gene in E. coli through Stabilization of Its . . . ", Proc. Natl. Acad. Sci., 76:5774-5778.
Twigg, A. J. and Sherratt, D. (1980), "Trans-Complementable Copy-Number Mutants of Plasmid ColE1", Nature, 283:216-218.
Simons, G. et al. (1984), "High-Level Expression of Human Interferon Gamma in E. coli Under Control of the PL Promoter . . . ", Gene, 28:55-64.
DeBoer, H. A. et al. (1982), "Construction of a Tandem Trp-Lac Promoter and a Hybrid Trp-Lac Promoter for Efficient . . . ", Promoters: Structure and Function, 462-481.

Primary Examiner—Delbert R. Phillips
Attorney, Agent, or Firm—Roman Saliwanchik; David R. Saliwanchik

[57] ABSTRACT

Hybrid useful proteins are prepared by a novel biological system comprising a prokaryotic host transformed with novel hybrid plasmids' β-glucuronidase (BG) gene DNA and the desired protein gene DNA. Specifically exemplified are plasmids which comprise BG gene DNA and protein A DNA. E. coli K-12 derivative hosts transformed with plasmid pBG3-2ΔN express >60% of the desired fusion protein having protein A-like biological activity. Other useful proteins can be expressed via the elegant highly efficient expression system of the subject invention.

3 Claims, 5 Drawing Figures

HYBRID PROTEINS PRODUCED BY AN ULTRAHIGH PROKARYOTIC EXPRESSION SYSTEM

BACKGROUND OF THE INVENTION

Expression level is one of the most important considerations in the utilization of cloned gene products. Elevated levels of protein expression have important ramifications both in terms of protein yield per fermentation volume and in degree of purification difficulty. Most efforts at increasing expression of cloned gene products have, to date, focused on the use of strong promoters in conjunction with an efficient ribosome binding site. A variety of promoters have been used to increase expression, the most commonly used being the $P_L$ promoter from phage lambda and the E. coli lacUV5 and trp promoters.

The lambda $P_L$ promoter has been successfully used in conjunction with a CI857 temperature-sensitive lambda repressor. This allows for low level expression of the cloned product during E. coli growth at 30° C. Once substantial cell density is established, the cloned gene can be derepressed by growth at 42° C. This method has been used in the expression of gene products lethal to the host cells. Several investigators have reported expression levels of 4% (Waldman, A. S., Haeusslein, E., and Milman, G. [1983] J. Bio. Chem. 258:11571-11575); 7% (Yoakum, G. H., Yeung, A. T., Mattes, W. B., and Grossman, L. [1982] PNAS 79:1766-1770; Derom, C., Gheysen, D., and Fiers, W., [1982] Gene, 17:45-54); and 13% (Oehmichen, R., Klock, G., Altschmied, L., and Hillen, W. [1984] EMBO J. 3:539-543) using the $P_L$ promoter under thermolabile represser control.

Recently, there has been increased use of a chimeric promoter consisting of sequences from the E. coli lacUV5 and trp promoters. This hybrid promoter is known as the tac promoter; it contains the −10 region from the lac promoter and the −35 region of trp. This hybrid promoter is repressed by the E. coli lac I$^q$ gene product and induced by 5 mM isopropyl-β-D-thiogalactopyranocide (IPTG). This system has been used by several investigators with varying results. Expression of various proteins have reached the 7% level (Bagdasarian, M. M., Amann, E., Lurz, R., Ruckert, B., and Bagdasarian, M. [1983] Gene 26:273-282); the 10% level (Bikel, I., Roberts, T. M., Bladon, M. T., Green, R., Amann, E. and Livingston, D. M. [1983] PNAS 80:906-910) and the 30% level (Amann, E., Brosius, J., and Ptashne, M. [1983] Gene 25:167-178).

Protein expression levels are dependent on the genetic background of the host cell. The utilization of host cells containing specific mutations has been shown to increase the level of a cloned protein. Two genes have received wide attention in this regard, the lon and pnp mutations.

The lon mutation has been mapped to the capR region of the E. coli genome and has been shown to code for an ATP-dependent protease (Shineberg, B. and Zipser, D., [1973] J. Bact. 116:1469-1471). This ATP-dependent protease is one of the eight proteases found in E. coli (Chung, C. H. and Goldberg, A. L. [1981] PNAS 78:4931-4935; Sreedhara Swamy, K. H. and Goldberg, A. L. [1981] Nature 292:652-654). It has been demonstrated to be the major protease involved in the degradation of proteins produced from missense and nonsense mutations (Mount, D. W. [1980] Ann Rev. Genet. 14:279-319). The pnp mutation has been mapped to the polyribonucleotide phosphorylase gene. Polyribonucleotide phosphorylase has been shown to be involved in the phosphorolysis of ribonucleic acid and therefore implicated in mRNA breakdown. Subsequent studies have shown a 20- to 100-fold increase in specific activity of cloned fungal catabolite dehydrogenase when cloned into pnp mutant strains (Hautala, J. A. Bassett, C. L., Giles, N. H. and Kushner, S. R. [1979] Proc. Natl. Acad. Sci. USA 76:5774-5778). These studies also demonstrated a 4- to 7-fold increase in plasmid copy number in these mutant strains. Thus the increase in enzyme-specific activity could be due to increased mRNA synthesis, increased mRNA lifetime, or a combination of both phenomena.

The rop (repressor of primer) gene has been known for some time to control plasmid copy number. In 1980, it was demonstrated that deletion of a non-essential region of E. coli, colE1 derived plasmids increases plasmid copy number. Deletion of this region increased plasmid DNA from 4% of chromosonal DNA to 20%. This deletion was trans recessive as coinfection of the host with a wild type plasmid reduced the copy number of the mutant plasmid. (Twigg, A. J. and Sherratt, D. [1980] Nature 283:216-218].

Recent prior art reports for E. coli expression systems, wherein proteins foreign to the E. coli host are produced, disclose expression levels of about 25 to 30% of total cellular protein. Simons et al. reported that human interferon gamma was expressed at levels up to 25% of total cellular protein. These workers utilized the $P_L$ promoter of phage lambda followed by the translational initiator region derived from either phage MS2 replicase or the E. coli tryptophan attenuator region (Simons, G., Remaut, E., Allet. B., Devos, R. and Fiers, W. [1984] Gene 28:55-64.) Amann at al. have expressed the lambda repressor as 30% of total cellular protein using the tac promoter system (Amman, E., Brosius, J. and Ptashne, M. [1983] Gene 25:167-178). As stated above this promoter contains the −10 region of the lacUV 5 promoter and the −35 region of the trp promoter (DeBoer, H. A., Comstock, L. J., Yansura, D. G. and Heynecker, H. L. in Promoters: Structure and Function, Praeger, New York [1982] 462-481 (R. L. Rodriguez and M. J. Chamberlin eds.)

BRIEF SUMMARY OF THE INVENTION

The subject invention concerns novel hybrid proteins which are produced with a novel biological system. The novel biological system comprises a prokaryotic host transformed with novel hybrid plasmids comprising β-glucuronidase gene DNA (BG) and the desired protein gene DNA. Specifically exemplified herein is the construction of novel hybrid plasmids denoted as plasmid pBG9, plasmid pBG5, plasmid pBG3-2, and plasmid pBG3-2ΔN. These plasmids comprise β-glucuronidase gene DNA and protein A DNA. When used to transform a suitable prokaryotic host, there is realized the production of protein A-like compounds, i.e., compounds which are indistinguishable from native protein A in the key biological function of binding IgG at the Fc region of the molecule. Advantageously, the expression of these hybrid proteins by the transformed host is considerably higher than realized with any known prokaryotic expression system. For example, the fusion (hybrid) proteins exemplified herein are produced at levels of greater than 45% of total E. coli cell protein in host cells containing either the lon or the pnp mutation. Also, advantageously, 100% of the expressed hybrid protein is found in the soluble cytosolic fraction upon disruption of the host cell. This result is in contrast to the experience of many skilled in the art who have found that relatively high expression (ca. 7%) of foreign proteins in *E. coli* resulted in production of an insoluble and inactive protein.

Plasmid pBG3-2ΔN exemplifies the ultimate of the ultrahigh prokaryotic expression system. Hosts transformed with this plasmid express >60% of the desired fusion protein. This ultrahigh level of expression is achievd by partially or totally deleting, or otherwise inactivating, the rop gene by constructing a ΔNde deletion in plasmid pBG3-2. This procedure can be used on any plasmid derived from the *E. coli* colEl plasmid usuable in the subject invention since all of these plasmids contain the rop region. Examples of such plasmids are pBR322, pBR325, and pHC79.

Plasmid pBG3-2ΔN can be used to make a BG/protein A fusion protein containing 18 amino acids of BG-derived sequences and exhibiting protein A activity, i.e., binding IgG at the Fc region of the molecule.

It is surprising that the *E. coli* host transformed with the novel hybrid plasmids of the subject invention expresses the fusion BG/protein A product in ultrahigh amounts in view of the known fact that BG is expressed in minute amounts by its native *E. coli* host. It is believed that this low level expression of BG by native *E. coli* has led persons skilled in the art away from using BG promoter DNA in prokaryotic expression systems. Rather, the lac and trp promoters have been extensively used in prokaryotic expression systems.

The expression system of the subject invention, as exemplified by fusion to the protein A gene or fragments thereof, can be used, advantageously, when fused to other genes encoding other useful proteins, e.g., interferons, interleukins, insulins, growth hormones, and industrial enzymes, e.g., amylases, proteases, and sugar isomerases, by following the procedures disclosed herein and attendant procedures known in the art.

DESCRIPTION OF THE DRAWINGS AND CHARTS

FIG. 1: This drawing depicts the construction of an intermediate plasmid from plasmid pAc37. Plasmid pAc37 comprises the protein A gene and the entire DNA of pBR322.

Figure 2:
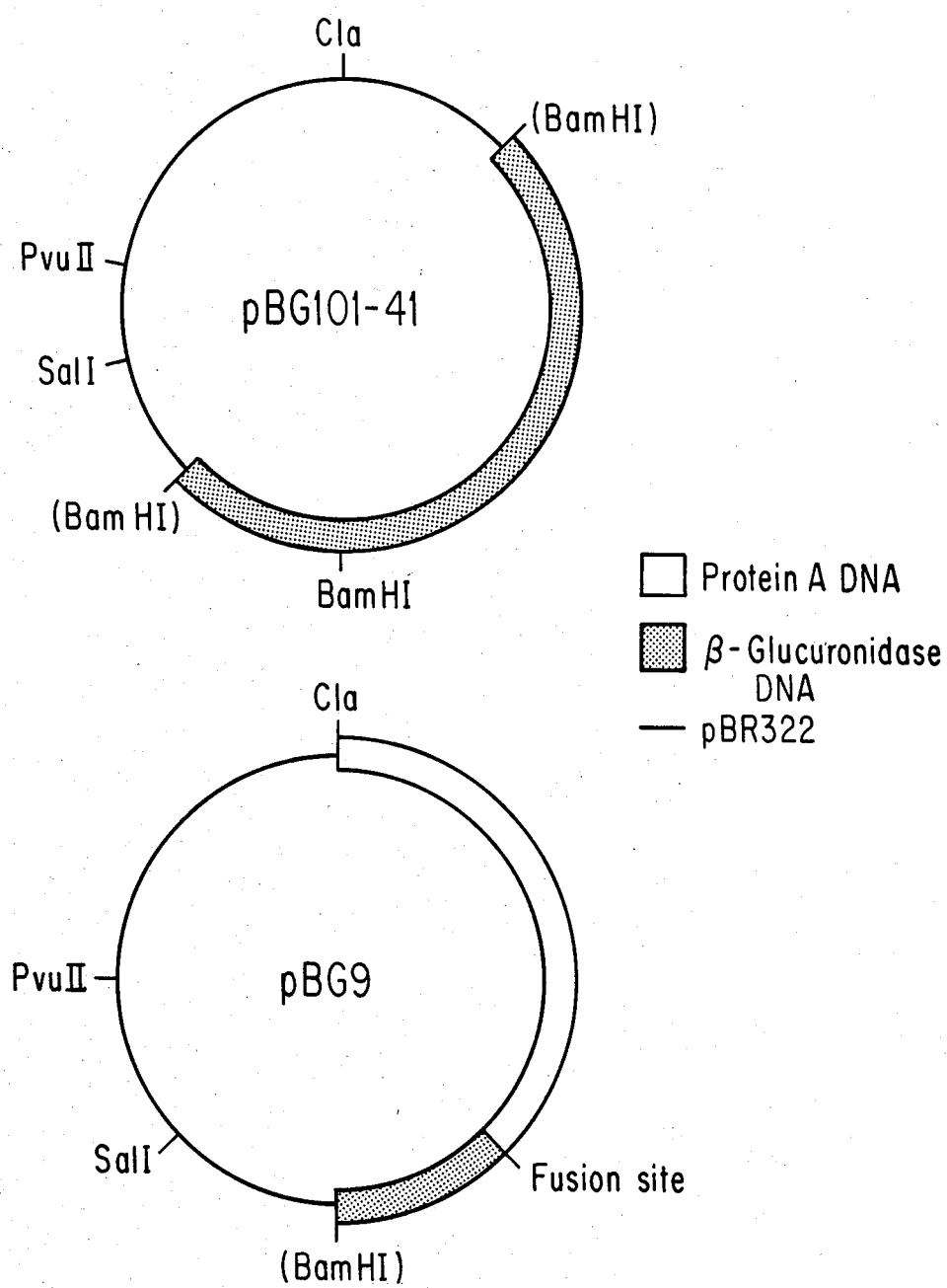

FIG. 2: Shown are the restriction maps with gene DNA inserts for plasmids pBG101-41 and pBG9. The BamHl sites which are not regenerated during the cloning are marked (BamHl).

Figure 3:
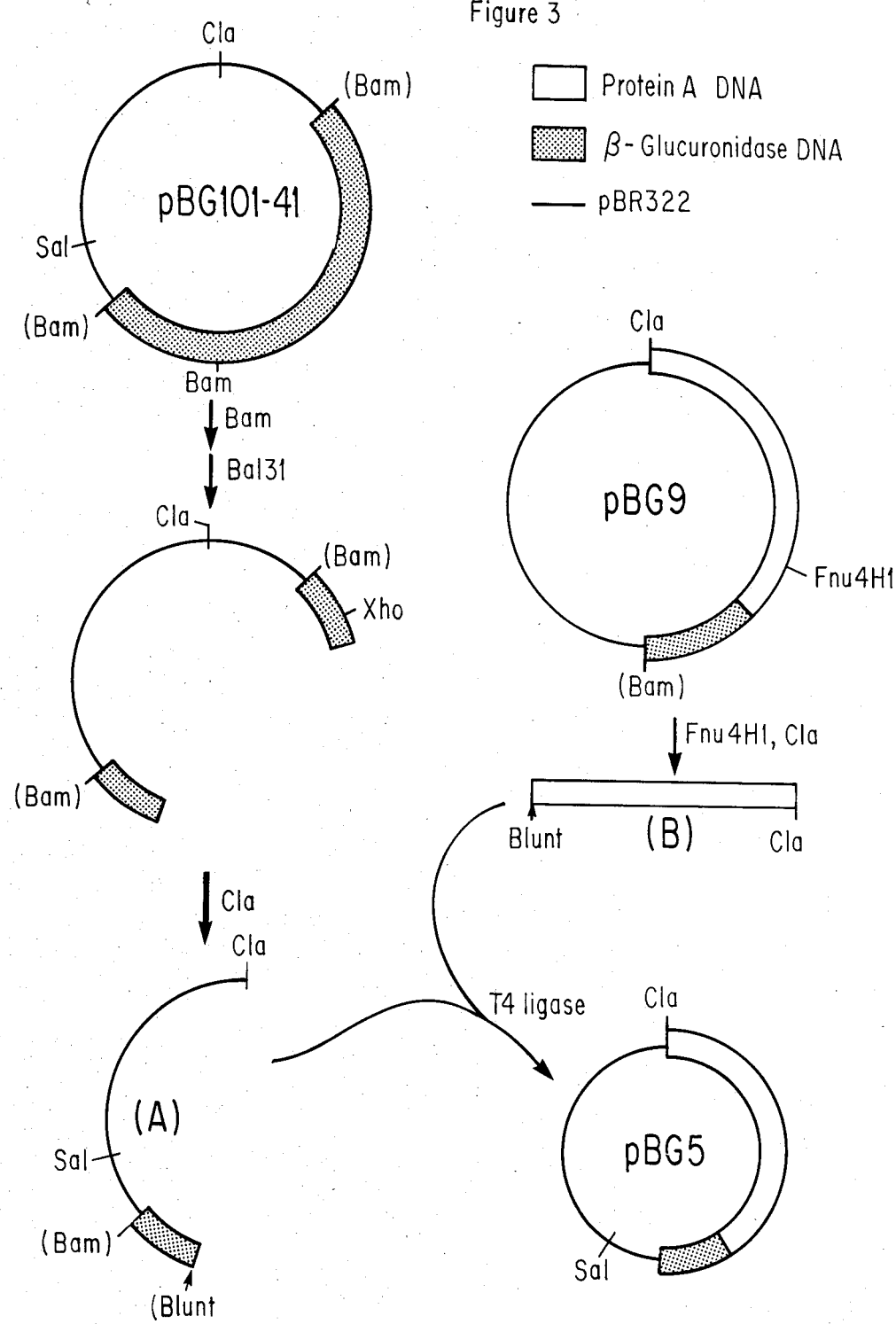

FIG. 3: The construction of plasmid pBG5 from plasmid pBG9 is shown.

Figure 4:
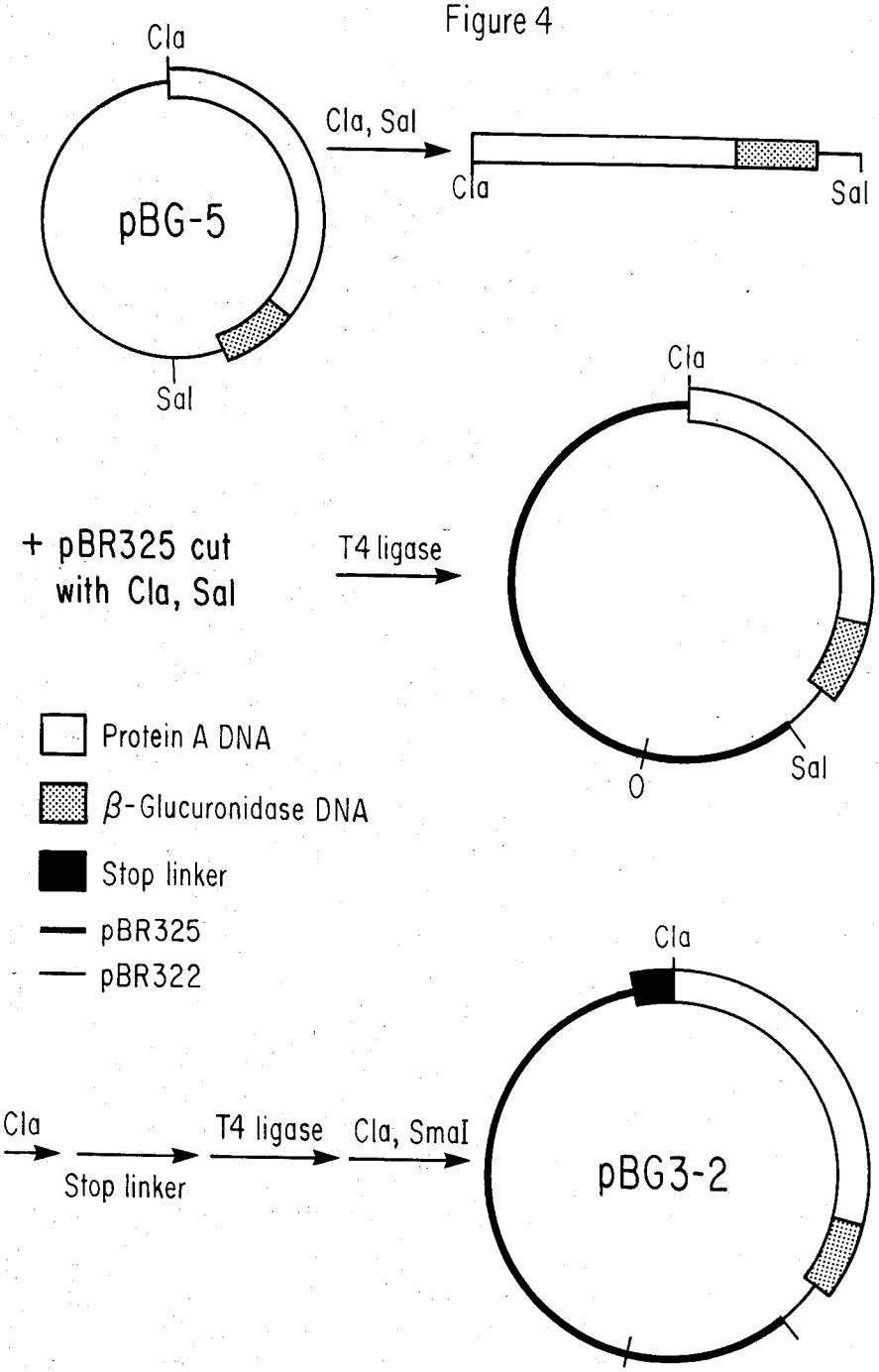

FIG. 4: The construction of plasmid pBG3-2 from pBG5 and plasmid pBR325 is shown.

Figure 5:
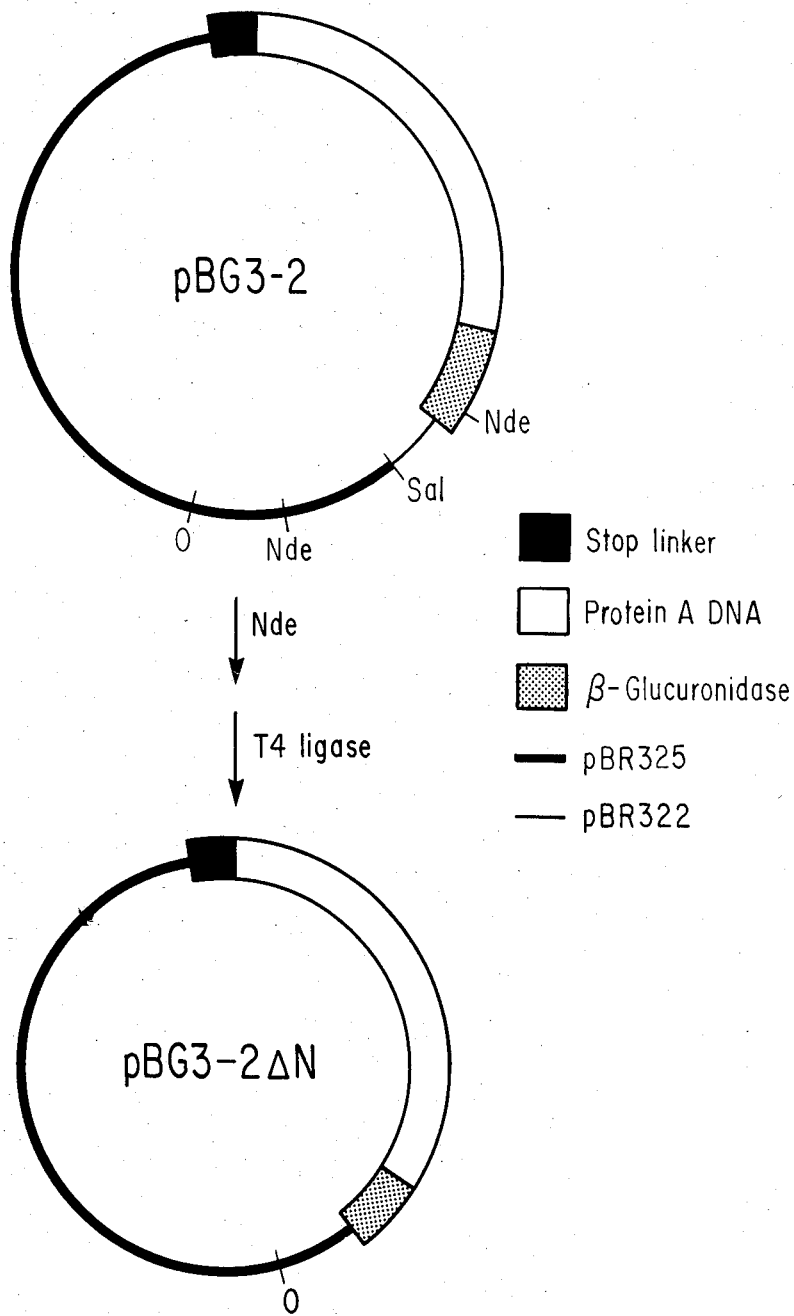

FIG. 5: The construction of plasmid pBG3-2ΔN from plasmid pBG3-2 is shown.

CHART A: Nucleotide sequence coding for the amino acid sequence of *Staphylococcus aureus* Protein A.

CHART B: Shown is the DNA sequence of hybrid plasmid pBG9 and the amino acid sequence of the expressed fusion protein.

CHART C: The DNA sequence of hybrid plasmid pBG5 and the amino acid sequence of the fusion protein expressed is shown.

CHART D: Shown is the DNA sequence of hybrid plasmid pBG3-2 and the amino acid sequence of the expressed fusion protein.

DETAILED DISCLOSURE OF THE INVENTION

Before detailing the construction and identity of the novel plasmids, proteins, and expression system of the subject invention, there is disclosed the Materials and Methods employed.

(1) Plasmid DNA preparation

Procedure used for large scale preparation of plasmid DNA was essentially as follows: A 250 ml culture was grown to Log phase, amplified with chloramphenicol at O.D. 0.6 to 0.7 (or alternatively with no chloramphenicol addition) and grown overnight. Cells were pelleted at 6K, 20 min. JA14 rotor, and resuspended in 6 ml glucose buffer (50 mM glucose, 25 mM tris, 10 mM EDTA). Cells were incubated 10 min at room temp in the presence of 1 ml of 20 mg/ml lysozyme freshly made; placed on ice with the addition of 13.8 ml 1% SDS in 0.2N NaOH for 5 min, and kept on ice an additional 15 min with 7 ml 5M KAC (pH 5.0-5.5). Debris was pelled at 10K for 10 min and supernate extracted once with an equal volume of phenol-chloroform-isoamyl alcohol (25:24:1, TE saturated, 0.1% 8-hydroxyquinoline). Following precipitation with 0.6 vol. isopropyl alcohol, DNA was purified over CsCl gradients.

(2) Restriction enzyme digestion and isolation of desired fragments

Digestions were carried out according to suppliers' instructions. Separation of fragments was achieved by agarose gel electrophoresis (described below). Electrophoresed DNA was purified and concentrated by passing over Elu-tip columns (Schleicher and Schuell, Keene, NH) according to supplier's instructions, followed by precipitation in 2.5 volumes EtOH with added carrier tRNA.

(3) Minilysate plasmid analysis

Transformed cells were inoculated into 1 ml of L-broth supplemented with either 10 μg/ml tetracycline or 50 μg/ml ampicillin and grown for 3-5 hr at 37° C. The cells were collected by centrifugation at 10,000xg for 15 min then resuspended in 50 μl of STET buffer (8% sucrose, 5% Triton X-100, 50 mM EDTA, 50 mM Tris-HCl pH 8.0). 50 μl of lysozyme solution (2 mg/ml in STET buffer) was added and the tubes were incubated for 4 min at room temperature, then heated to 100° C. for 3 min. The tubes were then cooled to 0° C. on ice. After 5 min at 0° C., the insoluble material was removed by centrifugation at 10,000xg for 15 min. An equal volume of ice cold isopropyl alcohol was added to the supernatant and the tubes were placed at 70° C. for 5 min. The DNA precipitate was collected by centrifugation at 10,000xg for 10 min and resuspended in 10-25 μl of TE buffer (10 mM tris-Cl, 0.1 mM EDTA pH 8.0). Restriction digest of the DNA was performed as described above using 5 μl of plasmid solution in a final volume of 15 μl containing 6.7 μg/ml of RNase A.

(4) DNA ligations

T4 ligase was used for both sticky and blunt end ligations, and was in each case present in excess (200 units/μg DNA). For sticky ends, incubation time was 2-4 hr at 16° C. and for blunt ends the time was increased to 16 hr. For standard vector/insert ligations, insert was present in a 5-fold molar excess with 0.02 pmoles of vector and 0.1 pmoles of insert in a 20 μl reaction volume. For the generation of deletion mutants by a unimolecular recircularisation reaction, plasmid was diluted to 1 μg/ml following restriction endonuclease digestion and ligated. Blunt-end ligation of linker was carried out with 100-fold molar excess of linker with the concentration of vector at 0.02 pmoles/20 μl reaction.

(5) Transformation

Fresh overnight cultures were diluted to L-broth and allowed to grow at 37° C. with agitation until an $A_{600}$ of 0.3 was obtained. The cells were chilled on ice, then collected by centrifugation (10 min at 4100xg). The cells were resuspended in ½ the original volume of ice cold 50 mM $CaCl_2$ and incubated on ice for 20 min. The cells were again collected by centrifugation as above and resuspended in ice cold 50 mM $CaCl_2$ (1/25 the original volume). 0.1 ml of the cell suspension was mixed with 1–10 μl (50–100 ng) of DNA plasmid solution and allowed to sit for 30 min at 0° C. The cells were then heated to 37° C. for 2 min and plated on L-broth plates containing 1.5% agar and either 10 μg/ml tetracycline or 50 μg/ml chloramphenicol when pBR325 derivatives are transformed. The plates were incubated overnight at 37° C. Transformation efficiencies of $1 \times 10^6$ colonies per μg plasmid DNA were routinely observed.

(6) Agarose electrophoresis

DNA fragments were isolated by gel electrophoresis in 0.8% agarose in 2X tris-borate buffer (178 mM tris, 178 mM boric acid, 5 mM $Na_2EDTA$ pH 8.4). Analytical and preparative gels were run in a horizontal gel box at 60 volts submerged in electrophoresis buffer (1X trisborate). DNA bands were visualized under UV light by including 5.0 μg/ml ethidium bromide (EtBr) in the gel. A slice containing the desired DNA band was cut from the gel and the DNA recovered by electrophoresis in 1X tris-borate buffer in a dialysis tube (½ in. diameter) containing 0.5–1.0 ml of buffer. Electrophoresis was carried out for 30 min at 10 volts or until the stained material was located against the side of the dialysis tubing. The gel slice was removed from the dialysis bag and the DNA recovered by repeatedly flushing the bag with tris-borate buffer. NaCl was added to the DNA solution to a final concentration of 1M and the ethidium bromide and agarose gel impurities were removed by two extractions with phenol saturated with tris burate buffer. The phenol was removed by two extractions with ether and the purified DNA was recovered by precipitation with 1/50 volume 5M NaCl and 2.5 volumes cold ethanol. The precipitation reaction was carried out at −70° C. for 15–20 min. The precipitated DNA was recovered by centrifugation at 10,000xg for 15 min. Yield of recovered fragment was assayed by direct comparison of ethidium bromide fluorescence with pure DNA standards. Typically, 50% recoveries were obtained with the yield decreasing as fragment size increased.

(7) Protein A radioassay

Protein A activity was determined by coating Dynatech Immunolin (Dynatech Diagnostics, Inc., South Windham, ME) 1 microtiter wells with 50 μl of a 1:10,000 dilution of normal rabbit serum (NRS) and incubating at room temperature for 4 hr. The NRS was shaken from the wells, which were then blocked with 1% ovalbumin in phosphate buffered saline (OVA/PBS) by incubation for 1 hr at 4° C. The wells were emptied; then 25 μl samples containing between 0.1 and 1,000 ng protein A were added to each well. A standard curve utilizing commercial protein A was run in each assay. All dilutions were in OVA/PBS. 25 μl of $^{125}$I-protein A (6,000 cpm) in OVA/PBS was added to each well and the plates were incubated for 16 hr at 37° C. in a sealed plastic container containing a small beaker of water. Following incubation, the wells were aspirated and washed 3X with PBS and once with water. The wells were dried and counted for 2 min in 2 ml Aquasol (New England Nuclear Corp., Boston, MA) in a Beckman model LS7000 beta counter (Beckman Instruments, Inc., Fullerton, CA).

(8) Protein A rocket immunoelectrophoresis

Protein A concentration and activity was determined by rocket immunoelectrophoresis in a 1% agarose gel containing 31 μg/ml human IgG in tris-glycine pH 8.6 buffer (3.75 g/l tris base, 7.5 g/l glycine). Protein A standards between 0.25 and 1.0 μg were run on every gel. Electrophoresis was allowed to proceed for 3 hr at 400 volts using tris-glycine as an electrophoresis buffer. Following electrophoresis, the gels were dried, then briefly stained with Coomassie blue and destained with 5% methanol, 10% acetic acid.

(9) Cell homogenization

Transformed cells were collected by centrifugation at 12,000xg for 5 min at 4° C. and resuspended in 0.5 volumes of HEPES (4-(2-hydroxyethyl)-1-piperazineethanesulfonic acid)/KCl/DTT (dithiothreitol) buffer (6 gm HEPES pH 8.0, 7.5 gm KCl, 0.15 gm DTT per liter). The cell suspension was digested with lysozyme at a final concentration of 300 μg/ml for 30 min at 37° C. The suspension was sonicated by two 5 min pulses at 300 watts on ice. Soluble protein was isolated by centrifugation at 25,000xg for 30 min at 4° C. The supernatant was removed and the precipitate was suspended in an equal volume of HEPES/KCL/DTT buffer. For experiments where total cell protein was run on SDS gels, the cells were solubilized by heating to 100° C. for 5 min in 5 volumes of SDS-homogenization buffer (50% v/v glycerol, 5% v/v 2-mercaptoethanol, 5% w/v sodium dodecyl sulfate, and 0.005 mg/ml pyronine Y).

(10) Polyacrylamide gel electrophoresis and Western analysis

All SDS gels were run by the method of Laemmli (Laemmli, U. K. [1970] Nature [London] 227:680–685). These gels contained a total acrylamide concentration of 12%. Slab gels were 1.5 mm wide, run in an electrophoretic apparatus obtained from Hoefer Scientific Instruments (San Francisco, CA). Tube gels were run in 6 mm i.d.×10 cm glass tubes without a stacking gel. Western blots were performed on nitrocellulose filters. Protein was transferred to the filters at 200 mA for 12 hr. The filters were blocked for 4 hr with 0.1% bovine serum albumin (BSA) in phosphate buffered saline (PBS) at room temperature and hybridized with either 10 uCi of [$I^{125}$]-IgG (NEN) or 100 μl of rabbit IgG conjugated with peroxidase at room temperature overnight with agitation. The blots were then washed 4X with PBS and exposed to Kodak XAR-5 x-ray film or developed with 25 mg diaminobenzidine in 100 ml PBS with 25 μl $H_2O_2$.

(11) Measurement of protein A content in cloned cells

Following fermentation, cells were homogenized in 20 mM tris-HCl pH 8.3 containing 0.5% Triton X-100 by vortexing with glass beads or in a DyanoMill model KDL-pilot bead mill (obtained from Impandex, Maywood, N.J.) operated at maximum speed and charged with 0.2 mm diameter glass beads. The homogenate was clarified by centrifugation at 16,000xg for 30 min and the supernatant protein concentration measured by the Lowery protein assay or by biuret. Protein A concentration was measured by rocket immunoelectrophoresis against human IgG.

(12) HPLC purification of proteins

Protein A and protease K were purified or assayed by HPLC using a Beckman model 360 gradient machine (Beckman Instruments, Inc.) fitted with a Waters μBondapak C18 column (Waters Associates, Milford, MA). Protein A was purified by a linear gradient between 10 mM sodium phosphate pH 7.2 (buffer A) and 60% v/v isopropanol 10 mM phosphate (buffer B). The column was eluted at a flow rate of 1 ml/min with a linear gradient between 0 and 100% buffer B over 80 min. Protease K was purified and protein A assayed in a similar manner except that buffer A contained 0.1% trifluoroacetic acid (TFA) and buffer B was 0.08% TFA in acetonitrile. The column was eluted at a flow rate of 2 ml/min by a linear gradient between 0 and 60% buffer B over 60 min.

(13) Fermentation

Fermentation was performed in a 20 l Chemapec fermentor (Chemapec, Inc., Woodbury, NY) fitted with $do_2$ and pH control. Recombinant cells were grown at a $do_2$ of 50% (air=100%) at the pH indicated. pH was adjusted by addition of 5M $NH_4OH$ or 5M $H_2SO_4$ as required. Foam was controlled by addition of antifoam B (E. I. du Pont De Nemours & Co., Inc., Wilmington, DE). Fermentation temperature was 37° C.; all fermentations were conducted with a final volume of 9.5 l.

(14) Bacterial strains and media

The source and genotype of all bacterial strains used are listed infra. All strains were maintained and grown using YT medium (8 gm/l tryptone, 5 gm/l yeast extract, and 5 gm/l sodium chloride).

(15) Chemicals

Nitrocellulose was obtained from Schleicher and Schuell (Keene, NH). Growth media were obtained from Difco (Detroit, MI). Acrylamide was obtained from Accurate Chemical & Scientific Corp., (Westbury, NY). Protein A standard was obtained from Pharmacia (Piscataway, NJ). All other chemicals were obtained from Sigma Chemical Co. (St. Louis, MO).

(16) Cultures (A) Bacterial

All E. coli strains disclosed herein are E. coli K-12 derivatives.

| Strains | Relevant Genotype | Repository Number |
|---|---|---|
| E. coli MS371 | F$^-$,Gal$^-$,Thi$^-$,endA sbcB,hsdR4 | NRRL B-15129 Deposited Aug. 18, 1982 and now available to the public upon request to the NRRL repository. |
| SG20251 | F$^-$,ara D139,lac, lon-100,Tn-10::cps E, str A,thi | NRRL B-15918 Deposited on Dec. 12, 1984. |
| PR13 | F$^-$,pnp-13,rna-19, thr-1,leu B6,thi-1, lac Y1,xyl-7,mtl-2, mal A1,strA132, (=rps L132) | Can be obtained from deposited cultures listed below by standard procedures. |

(B) Bacterial host containing plasmid

| Host | Repository Number |
|---|---|
| E. coli MS371(pAc37) | NRRL B-15127 Deposited on Aug. 18, 1982 and now available to the public upon request to the NRRL culture repository. |
| MS371(pBG101-41) | NRRL B-15905 |
| PR13(pBG9) | Deposited on Nov. 1, 1984 NRRL B-15907 |
| PR13(pBG5) | Deposited on Nov. 20, 1984 NRRL B-15908 |
| PR13(pBG3-2) | Deposited on Nov. 20, 1984 NRRL B-15909 |
| PR13(pBG3-2ΔN) | Deposited on Nov. 20, 1984 NRRL B-15910 Deposited on Nov. 20, 1984 |

(C) Plasmids

Plasmid pBR322 is a well-known and available plasmid. It is maintained in the E. coli host ATCC 37017. Purified pBR322 DNA can be obtained as described in Bolivar, F., Rodriquez, R. L., Greene, P. J. Betlach, M. C., Heyneker, H. L., Boyer, H. W., Crosa, J. H. and Falkow, S. (1977) Gene 2:95–113; and Sutcliffe, J. G. (1978) Nucleic Acids Res. 5:2721–2728. Plasmid pBR325 is also a well-known plasmid. It can be obtained from BRL Inc., P.O. Box 6009, Gaithersburg, MD 20877.

NRRL B-15907, NRRL B-15908, NRRL B-15909, NRRL B-15910, and NRRL B-15918 are available to the public upon the grant of a patent which discloses these accession numbers. It should be understood that the availability of these deposits does not constitute a license to practice the subject invention in derogation of patent rights granted for the subject invention by governmental action. The culture deposits are in the permanent collection of the Northern Regional Research Laboratory (NRRL), U.S. Department of Agriculture, Peoria, Ill., USA.

There are other well-known E. coli hosts which can be used instead of E. coli PR13, for example, E. coli MS371, HB101, and E. coli GMS407 (Novel, M. and Novel, G. [1973] Mol. Gen. Genet. 120:319).

Further, other prokaryotic hosts which can be used are microbes from the genera Salmonella, Pseudomonas, Bacillus, Streptomyces, and the like.

(17) Isolation of recombinant plasmid DNA from transformed host

Recombinant plasmid DNA can be isolated from its prokaryotic host by well-known procedures, e.g., using cleared lysate-isopycnic density gradient procedures, and the like.

(18) DNA sequencing

DNA sequence determination was carried out as described by Maxam and Gilbert (Maxam, A. and Gilbert, W. [1977] Proc. Nat'l. Acad. Sci. USA 74:560) and Heidecker et al. (Heidecker, G., Messing, J., and Gronenborn, B. [1980] Gene 10:69)

Construction of hybrid protein genes

The construction of the hybrid protein genes, exemplified herein as representative of the invention, was initiated with the use of plasmid pBG101-41. This plasmid contains approximately 6 kb of E. coli β-glucuronidase gene DNA inserted at the BamH1 site of plasmid pBR322. Plasmid pBG101-41 was cut with restriction endonuclease BamH1 and blunted by brief treatment with Bal-31 exonuclease. This exonuclease treatment removed 12 bases and left a blunt end.

DNA for insertion into the cut and blunted pBG101-41 was obtained from plasmid pAc37 which contains the *Staphylococcus aureus* protein A gene in pBR322. See FIG. 1 of the Drawing.

The cut and blunted plasmid pBG101-41 was ligated with the blunt-ClaI protein A fragment to give hybrid plasmid pBG9. Plasmid pBG9 contains 501 nucleotides coding for the N-terminal 167 amino acids of the β-glucuronidase protein fused to the protein A gene. See FIG. 2 of the Drawing.

Hybrid plasmid pBG5 was constructed from hybrid plasmid pBG101-41 and hybrid plasmid pBG9. See FIG. 3 of the Drawing. Plasmid pBG101-41 was cut with BamH1 and then digested with Bal-31 exonuclease (IBI-fast Bal-31). The resulting DNA was digested with ClaI: and insert DNA, prepared as disclosed infra, was ligated.

The insert DNA for the above ligation, containing the mature protein A coding sequences, was prepared from hybrid plasmid pBG9 by cutting this plasmid with the restriction enzymes ClaI and Fnu4H1.

The insert and vector DNA were ligated and transformed into *E. coli* strain PR13, and plasmid DNA was prepared from the transformants. A clone, labelled pBG5, contained the predicted restriction profile. Sequence analysis of this clone by the standard M13 method revealed that 18 amino acids of the BG coding sequence remained.

Hybrid plasmid pBG3-2 was constructed from plasmid pBG5 and plasmid pBR325. See FIG. 4 of the Drawing. Plasmid pBG3-2 contains the same DNA as plasmid pBG5 except that pBG5 contains pBR322 DNA and pBG3-2 contains pBR325 DNA; also, pBG3-2 contains a stop codon linker at the ClaI site at the end of the protein A gene DNA. The constructed linker segment of DNA contained stop codons in all three reading frames. It was inserted into the ClaI site in the pBG3-2 construction to insure that the final hybrid protein product did not contain any pBR325-derived amino acids.

Increased expression of the hybrid protein encoded by the fused gene in plasmid pBG3-2 was obtained by constructing a ΔNde deletion, i.e., by removing the DNA between the Nde site in pBR325 and the Nde site on the BG sequence. This deletion removed the bulk of the rop gene in pBR325, as well as the first 230 bases of the BG promoter region. This construction is identified as plasmid pBG3-2ΔN. When an *E. coli* host is transformed with pBG3-2ΔN, the host expresses protein A at levels >60% of total *E. coli* protein. In comparison, protein A is expressed in *E. coli* at 50% of total cellular protein in host cells containing the plasmid pBG3-2.

Utility of protein A

Protein A is widely used as an immunoabsorbent in a variety of diagnostic and basic research test systems. See U.S. Pat. No. 4,322,274. Recent interest in applications of protein A has centered around its possible clinical use in anticancer treatment. Sensitized peripheral blood lymphocytes, normally responsible for cytotoxicity of tumor cells, are hypothesized to be inhibited in this function by serum blocking factors which are presumed to consist of specific antigens, antibodies, antiglobulins, and immune complexes. See Barnes, B. C. (1981) Cancer Bull. 33:278. These "blocking" factors can be removed from sera of tumor-bearers by absorption to *S. aureus,* Cowan I cells which contain protein A, and thus allow cell-mediated tumor cell toxicity to proceed in in vitro test systems. See Steele, G., Ankerst, J., and Sjogren, H. (1974) Int. J. Cancer 14:83. Protein A also activates polyclonal antibody synthesis independent of its IgG binding activity. See Sjodahl, J. and Moller, G. (1979) Scand. J. Immunol. 10:593.

Extensive testing of protein A as an anticancer agent has been inhibited by the high cost of the material and by the presence of impurities in some protein A preparations. Should the cost of protein A preparations be significantly reduced and the purity improved, then further clinical testing of protein A for anticancer uses would proceed more rapidly.

Having the data disclosed herein, those skilled in the art can readily appreciate the identity of other equivalent nucleotide sequences coding for molecules with substantially the same protein A-like biological activity. Thus, the scope of the subject invention includes not only the specific nucleotide sequence depicted above, but also all equivalent nucleotide sequences coding for molecules with substantially the same identifiable protein A-like biological activity. The term "equivalent" is being used in its ordinary patent usage here as denoting a nucleotide sequence which performs substantially as the nucleotide sequence identified herein to produce molecules with substantially the same identifiable protein A-like biological activity in essentially the same kind of hosts. Within this definition are subfragments of the protein A-like material which have the property of binding to IgG at the Fc region, or subfragments which have polyclonal B-cell activating activity. Plasmid pAc37, disclosed in Example 1, contains the entire nucleotide sequence coding for the amino acid sequence of *Staphylococcus aureus* protein A. This sequence, which is shown in Chart A, enables persons in the art to obtain cloned nucleotide sequences coding for identifiable protein A-like material and identifiable subfragments of protein A-like material, as defined above. The identifiable protein A-like material of the subject invention, and identifiable protein A-like subfragments thereof, can be used in the same manner as protein A, disclosed above.

Following are examples which illustrate procedures, including the best mode, for practicing the invention. These examples should not be construed as limiting. All percentages are by weight and all solvent mixture proportions are by volume unless otherwise noted.

EXAMPLE 1

Construction of Hybrid Plasmid pBG9 from Plasmid pBG101-41 and Plasmid pAc37 and Expression of Fusion Protein A Product The plasmid pBG9 containing the β-glucuronidase promoter and the β-glucuronidase-protein A hybrid gene was constructed from the plasmid pBG101-41 and the blunt-ClaI protein A fragment described herein. Plasmid pBG101-41 was opened at the unique BamHI site (located 179 amino acids after the initiation methionine) and blunted by brief treatment with Bal-31 exonuclease (as described by manufacturer). This exonuclease treatment removed 36 bases (12 amino acids) and left a blunt end. The plasmid was further cut with ClaI at the unique site in plasmid pBR322.

Plasmid pAc37 contains the protein A gene in pBR322. Plasmid pAc37 was digested with Rsa which cleaves the protein A gene at position 65 and 1264 after the TTG start codon (T=1). The 1199 base pair Rsa fragment was isolated by agarose electrophoresis. ClaI linkers (New England Biolabs, Beverly, MA, sequence CATCGATG) were fused to the isolated Rsa fragment.

This construction was cut with ClaI and inserted into the ClaI site of pBR322 to form an intermediate plasmid designated pA1. Plasmid pA1 was partially digested with ClaI and the ClaI sticky end filled in in a reaction containing 2 mM each of the 4 deoxynucleotide triphosphates and 5 units of the Klenow fragment of *E. coli* DNA polymerase 1 in 25 μl of 50 mM tris-Cl pH 7.2, 10 mM Mg₂SO₄, 0.1 mM DTT, 50 μg/ml BSA and 1 μg of the restriction fragment. The fill-in reaction was incubated for 20 min at 22° C. and stopped by heat inactivation at 70° C. for 10 min. The plasmid was then digested with SalI and the 1826 base pair fragment isolated by agarose electrophoresis. This fragment was further cut with ClaI and inserted into the cut plasmid described above. (See FIG. 1 of the Drawing.)

The DNA sequence of plasmid pBG9 and the amino acid sequence of the fusion protein expressed by *E. coli* PR13(pBG9) is shown in Chart B.

EXAMPLE 2

Plasmid pBG9 and Plasmid pBG101-41 and Expression of Fusion Protein A Product

The plasmid pBG101-41 consists of pBR322 which has been opened at the BamHI site with insertion of the SauI partial sequences containing the BG promoter and BG coding domains. Plasmid pBG101-41 was cut with BamHI, which cleaves this plasmid at a site 179 amino acids after the methionine start codon, then digested with Bal-31 exonuclease (IBI-fast Bal-31) at an enzyme concentration of 20 U/ml and a DNA concentration of 100 μg/ml. The reaction was allowed to proceed at 30° C. At 10 min, 15 min, and 20 min one-third of the digest was removed and the reaction halted by addition of EDTA to 20 mM, followed by freezing at −80° C. The time points were individually extracted with phenolether and precipitated with ethanol. The DNA was digested with ClaI, which cuts in the unique site in pBR322; then insert DNA was ligated.

Insert DNA containing the mature protein A coding sequences was prepared from the plasmid pBG9. This plasmid was cut with the restriction enzymes ClaI and Fnu4H1. Restriction endonuclease Fnu4H1 cuts the protein A gene one base to the 5' end of the signal peptide cleavage point and ClaI cuts the gene in the C-terminal repeating domains. This ClaI site was constructed by ligating a ClaI linker at the Rsa site located 284 base pairs from the 3' end of the protein A gene.

Insert and vector DNA were ligated together in a 4:1 insert to vector ratio in a reaction containing 20 μg/ml vector DNA. The T4 ligase-catalyzed reaction was allowed to proceed overnight at 15° C.; then ligase was inactivated by heating to 70° C. for 15 min. The reaction mixture was digested with Xho (which cuts at a unique site in the BG protein) to prevent transformation of any plasmids containing a BG deletion. The reaction mixture was transformed into *E. coli* strain PR13 and plasmid DNA was prepared from the transformants. A clone, labelled pBG5, contained the predicted restriction profile. Sequence analysis of this clone by the M13 method revealed that 18 amino acids of the BG coding sequence remained. (See FIG. 3 of the Drawing.)

The DNA sequence of plasmid pBG5 and the amino acid sequence of the fusion protein expressed by *E. coli* PR13(pBG5) is shown in Chart C.

EXAMPLE 3

Construction of Hybrid Plasmid pBG3-2 from Plasmid pBG5 and Plasmid pBR325 and Expression of Fusion Protein A Product Plasmid pBR325 was digested with ClaI and SalI and the 5368 base pair fragment containing the bulk of the plasmid coding sequences was isolated by agarose electrophoresis. Plasmid pBG5 was also digested with ClaI and SalI and the 2000 base pair fragment containing the BG promoter and the protein A coding sequences was isolated by agarose electrophoresis. These two DNA fragments were mixed in an equal molar ratio at 30 μg/ml per fragment and ligated with T4 ligase. The resulting product was digested with ClaI and the resulting linear molecule of 7.4 kb was isolated by agarose electrophoresis. A linker DNA fragment containing the stop codons, prepared as described in Example 4, was added in large molar excess and the reaction ligated with T4 ligase overnight at 15° C. The closed circular plasmid was digested with ClaI and SmaI to linearize plasmids containing multiple or no stop linkers, then transformed into *E. coli* PR13. (See FIG. 4 of the Drawing.)

The DNA sequence of plasmid pBG3-2 and the amino acid sequence of the fusion protein expressed by *E. coli* PR13(pBG3-2) is shown in Chart D.

EXAMPLE 4

Construction of A Stop Linker

A linker segment of DNA containing stop codons in all three reading frames was inserted into the ClaI site in the pBG3-2 construction to insure that the final product did not contain any pBR-derived amino acids. A synthetic DNA segment with the sequence CGGGCGCGCTAGCTAGCTAGCGCGCC was synthesized using an Applied Biosystems DNA synthesis machine Model 380A (Foster City, CA) by the procedure suggested by the manufacturer. This sequence is self annealing and yields the double stranded DNA fragment:

| C | G | G | G | C | G | C | G | C | T | A | G | C | T | A | G | C | T | A | G | C | G | C | G | C | C |   |
|---|---|---|---|---|---|---|---|---|---|---|---|---|---|---|---|---|---|---|---|---|---|---|---|---|---|---|
|   | C | C | G | C | G | C | G | A | T | C | G | A | T | C | G | A | T | C | G | C | G | C | G | G | G | C | which contains the stop sequences CTAGCTAGCTAG and the BssHI site: GCGCGC at both ends of the triphasic stop

EXAMPLE 5

Construction of Plasmid pBG3-2ΔN from Plasmid pBG3-2

Plasmid pBG3-2 was digested with restriction endonuclease Nde and the cut plasmid extracted with phenolether and precipitated with ethanol. The plasmid was religated at dilute DNA concentration (12 μg/ml) to favor intermolecular recircularization without incorporation of the Nde fragment to give plasmid pBG3-2ΔN. The reaction mix was transformed into *E. coli* PR13 and the colonies assayed by minilysate analysis. See FIG. 5 of the Drawings.

EXAMPLE 6

Transformation of plasmids pBG3-2, pBG3-2ΔN, pBG9 and pBG5 into *E. coli* PR13 or *E. coli* SG20251

*E. coli* PR13 or *E. coli* SG20251 were harvested from fresh overnight cultures grown as described in (5) Transformation.

The cells were made competent for transformation by treatment with CaCl$_2$ as described.

Plasmid DNA was prepared from cells harboring the plasmid by the methods described in (1) Plasmid DNA preparation.

0.1 ml of the competent cells were mixed with 50–100 ng of plasmid DNA for 30 min at 0° C. The cells were heated to 37° C. for 2 min then plated on L-broth plates containing 1.5% agar and either 10 μg/ml tetracycline or 50 μg/ml chloramphenicol when pBR325 derivatives are transformed. The plate were incubated overnight at 37° C. Transformation efficiencies of 1×10$^6$ colonies per μg plasmid DNA were routinely observed.

EXAMPLE 7

Fermentation of *E. coli* PR13(pBG3-2)

*E. coli* PR13(pBG3-2) can be grown by any of a number of methods familiar to those skilled in the art. This organism will grow on any complex medium capable of supporting the growth of *E. coli* and on any defined medium if such defined medium contains sufficient growth factors and metabolites necessary to support cell growth. In general these defined media comprise those capable of supporting the growth of *E. coli* if they contain the amino acids threonine and leucine. Production of recombinant protein by this organism is subject to catabolite repression. Thus, when protein production is desired, care must be taken that the growth medium does not contain glucose or any substance capable of causing catabolite repression. Catabolite repression in *E. coli* is mediated by an intercellular decrease in the levels of cAMP. Thus, this organism can be grown in the presence of growth media containing glucose if those media contain a high level of cAMP, typically 4 mM, or if those media contain high levels of a lipid soluble cAMP derivative, for example, dibuterylcyclic AMP at a concentration of about 10 μM.

In general, high levels of protein A can be produced by preparing an inoculum from a frozen stock of *E. coli* PR13(pBG3-2), which was streaked on YT/Cm medium and grown overnight. YT contains 8 g/l yeast extract, 5 g/l tryptone and 5 g/l NaCl. YT/Cm contains 50 mg/l chloroamphenicol. A colony was picked from this plate and inoculated into 10 ml of YT/Cm which has grown at 37° C. for 6–12 hr then inoculated directly into the fermenter.

*E. coli* PR13(pBG3-2) was grown in a 201 Chemapec fermenter (Chemapec, Woodbury, NY) charged with 9.8 l of 5 gm/l yeast extract and 5 gm/l tryptone. The dissolved oxygen concentration is maintained at about 50% (air=100%) and the pH was maintained at about pH 6.8 by automatic addition of 5M NaOH or 5M H$_2$SO$_4$. The normal inoculum volume is about 10 ml. With this inoculum, the fermenter can be harvested after 9 hr of growth. When cells are grown in this manner, 46% of the total *E. coli* derived protein produced in the fermenter is protein A.

Evidence demonstrates that cloned protein A is expressed in an active form. A Western blot probed with [$^{125}$I] labelled rabbit IgG shows that the hybrid protein has IgG binding activity even after treatment with hot SDS solution and electrophoresis in SDS-polyacrylamide gels.

The specific activity of soluble protein A extracted from the pnp-host strain was determined by radioassay (see (6) Protein A radioassay). This assay demonstrated that cell cytosol had protein A activity which was 35% of the specific activity of pure commercial material. Protein A concentration in this cytosolic preparation was determined to be 35% by SDS gel electrophoresis, indicating that the cloned material has essentially identical specific activity with the naturally occurring protein.

EXAMPLE 8

Fermentation of *E. coli* PR13(pBG3-2ΔN

When the recombinant organism is grown in a fermenter as described in (13) Fermentation, like plasmid pBG3-2, plasmid pBG3-2ΔN is subject to catabolite repression. The media and conditions described for *E. coli* PR13(pBG3-2) can be used to grow this organism as well. Surprisingly, *E. coli* containing plasmid pBG3-2ΔN produces an extraordinarily high level of recombinant product.

The following table shows the protein A expression levels of pBG9, pBG3-2 and pBG3-2ΔN:

| | Protein A Expresssion Levels | |
|---|---|---|
| | No. of BG Amino Acids | Expression Level* |
| pBG9 | 168 | 46% |
| pBG3-2 | 18 | 50% |
| pBG3-2ΔN | 18 | 73% |

*Protein A as percent of soluble cell protein. Protein A content is determined by Rocket immunoelectrophoresis and total protein by biuret.

EXAMPLE 9

Isolation of Host Transformed with a Plasmid

The host microbe, e.g., *E. coli* PR13, can be recovered minus the plasmid, e.g., pBG9, with which it was transformed, by standard procedures. For example, the transformed host can be grown in YT medium containing 0.01% w/v SDS to eject the plasmid from the host. Host cells without plasmid can be screened because of the loss of resistance to chloramphenicol and/or ampicillin.

As is well known in the art, the amino acid sequence of a protein, e.g., protein A, is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATH | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCL | Arginine (Arg) | WGZ |
| Tyrosine (Tyr) | TAK | Glycine (Gly) | GGL |
| Termination signal | TAJ | | |

-continued

| Termination signal | TGA |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.
A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T
J = A or G
K = T or C
L = A, T, C or G
M = A, C or T The above shows that the novel amino acid sequence of the fused protein A product, and other useful proteins, can be prepared by equivalent nucleotide sequences encoding the same amino acid sequence of the proteins. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kézdy, F. J. [1984] Science 223: 249–255).

The work described herein was all done in conformity with physical and biological containment requirements specified in the NIH Guidelines.

CHART A

TTG AAA AAG AAA AAC ATT TAT TCA ATT CGT AAA CTA GGT GTA GGT ATT GCA TCT GTA ACT TTA GGT
Met Lys Lys Lys Asn Ile Tyr Ser Ile Arg Lys Leu Gly Val Gly Ile Ala Ser Val Thr Leu Gly

ACA TTA CTT ATA TCT GGT GGC GTA ACA CCT GCT GCA AAT GCT GCG CAA CAC GAT GAA GCT CAA CAA
Thr Leu Leu Ile Ser Gly Gly Val Thr Pro Ala Ala Asn Ala Ala Gln His Asp Glu Ala Gln Gln
|—E—>

AAT GCT TTT TAT CAA GTG TTA AAT ATG CCT AAC TTA AAC GCT GAT CAA CGT AAT GGT TTT ATC CAA
Asn Ala Phe Tyr Gln Val Leu Asn Met Pro Asn Leu Asn Ala Asp Gln Arg Asn Gly Phe Ile Gln

AGC CTT AAA GAT GAT CCA AGC CAA AGT GCT AAC GTT TTA GGT GAA GCT CAA AAA CTT AAT GAC TCT
Ser Leu Lys Asp Asp Pro Ser Gln Ser Ala Asn Val Leu Gly Glu Ala Gln Lys Leu Asn Asp Ser

CAA GCT CCA AAA GCT GAT GCG CAA CAA AAT AAG TTC AAC AAA GAT CAA CAA AGC GCC TTC TAT GAA
Gln Ala Pro Lys Ala Asp Ala Gln Gln Asn Lys Phe Asn Lys Asp Gln Gln Ser Ala Phe Tyr Glu
<—E—|—D—>

ATC TTG AAC ATG CCT AAC TTA AAC GAG GAG CAA CGC AAT GGT TTC ATT CAA AGT CTT AAA GAC GAT
Ile Leu Asn Met Pro Asn Leu Asn Glu Glu Gln Arg Asn Gly Phe Ile Gln Ser Leu Lys Asp Asp

CCA AGC CAA AGC ACT AAC GTT TTA GGT GAA GCT AAA AAA TTA AAC GAA TCT CAA GCA CCG AAA GCT
Pro Ser Gln Ser Thr Asn Val Leu Gly Glu Ala Lys Lys Leu Asn Glu Ser Gln Ala Pro Lys Ala
<—D—|—A—>

GAC AAC AAT TTC AAC AAA GAA CAA CAA AAT GCT TTC TAT GAA ATC TTG AAC ATG CCT AAC TTG AAC
Asp Asn Asn Phe Asn Lys Glu Gln Gln Asn Ala Phe Tyr Glu Ile Leu Asn Met Pro Asn Leu Asn

GAA GAA CAA CGC AAT GGT TTC ATC CAA AGC TTA AAA GAT GAC CCA AGT CAA AGT GCT AAC CTT TTA
Glu Glu Gln Arg Asn Gly Phe Ile Gln Ser Leu Lys Asp Asp Pro Ser Gln Ser Ala Asn Leu Leu

GCA GAA GCT AAA AAG TTA AAT GAA TCT CAA GCA CCG AAA GCT GAT AAC AAA TTC AAC AAA GAA CAA
Ala Glu Ala Lys Lys Leu Asn Glu Ser Gln Ala Pro Lys Ala Asp Asn Lys Phe Asn Lys Glu Gln
<—A—|—B—>

CAA AAT GCT TTC TAT GAA ATC TTA CAT TTA CCT AAC TTA AAT GAA GAA CAA CGC AAT GGT TTC ATC
Gln Asn Ala Phe Tyr Glu Ile Leu His Leu Pro Asn Leu Asn Glu Glu Gln Arg Asn Gly Phe Ile

-continued
CHART A CAA AGC TTA AAA GAT GAC CCA AGC CAA AGC GCT AAC CTT TTA GCA GAA GCT AAA AAG CTA AAT GAT
Gln Ser Leu Lys Asp Asp Pro Ser Gln Ser Ala Asn Leu Leu Ala Glu Ala Lys Lys Leu Asn Asp GCA CAA GCA CCA AAA GCT GAC AAC AAA TTC AAC AAA GAA CAA CAA AAT GCT TTC TAT GAA ATT TTA
Ala Gln Ala Pro Lys Ala Asp Asn Lys Phe Asn Lys Glu Gln Gln Asn Ala Phe Tyr Glu Ile Leu
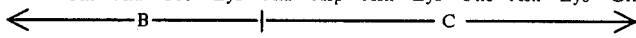

CAT TTA CCT AAC TTA ACT GAA GAA CAA CGT AAC GGC TTC ATC CAA AGC CTT AAA GAC GAT CCT TCA
His Leu Pro Asn Leu Thr Glu Glu Gln Arg Asn Gly Phe Ile Gln Ser Leu Lys Asp Asp Pro Ser

GTG AGC AAA GAA ATT TTA GCA GAA GCT AAA AAG CTA AAC GAT GCT CAA GCA CCA AAA GAG GAA GAC
Val Ser Lys Glu Ile Leu Ala Glu Ala Lys Lys Leu Asn Asp Ala Gln Ala Pro Lys Glu Glu Asp

AAC AAC AAG CCT GGT AAA GAA GAC GGC AAC AAA CCT GGT AAA GAA GAC GGC AAC AAA CCT GGT AAA
Asn Asn Lys Pro Gly Lys Glu Asp Gly Asn Lys Pro Gly Lys Glu Asp Gly Asn Lys Pro Gly Lys

GAA GAC AAC AAA AAC CTT GGC AAA GAA GAC GGC AAC AAA CCT GGT AAA GAA GAC AAC AAA AAA CCT
Glu Asp Asn Lys Asn Leu Gly Lys Glu Asp Gly Asn Lys Pro Gly Lys Glu Asp Asn Lys Lys Pro

GGC AAA GAA GAT GCC AAC AAA CCT GGT AAA GAA GAC GGC AAC AAG CCT GGT AAA GAA GAT GGC AAC
Gly Lys Glu Asp Gly Asn Lys Pro Gly Lys Glu Asp Gly Asn Lys Pro Gly Lys Glu Asp Gly Asn

AAA CCT GGT AAA GAA GAT GGC AAC AAG CCT GGT AAA GAA GAT GGC AAC AAG CCT CGT AAA GAA GAC
Lys Pro Gly Lys Glu Asp Gly Asn Lys Pro Gly Lys Glu Asp Gly Asn Lys Pro Gly Lys Glu Asp

GGC AAC GGA GTA CAT GTC GTT AAA CCT GCT GAT ACA GTA AAT GAC ATT GCA AAA GCA AAC GGC ACT
Gly Asn Gly Val His Val Val Lys Pro Gly Asp Thr Val Asn Asp Ile Ala Lys Ala Asn Gly Thr

ACT GCT GAC AAA ATT GCT GCA GAT AAC AAA TTA GCT GAT AAA AAC ATG ATC AAA CCT GGT CAA GAA
Thr Ala Asp Lys Ile Ala Ala Asp Asn Lys Leu Ala Asp Lys Asn Met Ile Lys Pro Gly Gln Glu

CTT GTT GTT GAT AAG AAG CAA CCA GCA AAC CAT GCA GAT GCT AAC AAA GCT CAA GCA TTA CCA GAA
Leu Val Val Asp Lys Lys Gln Pro Ala Asn His Ala Asp Ala Asn Lys Ala Gln Ala Leu Pro Glu

ACT GGT GAA GAA AAT CCA TTC ATC GGT ACA ACT GTA TTT GGT GGA TTA TCA TTA GCG TTA GGT GCA
Thr Gly Glu Glu Asn Pro Leu Ile Gly Thr Thr Val Phe Gly Gly Leu Ser Leu Ala Leu Gly Ala

GCG TTA TTA GCT GGA CGT CGT CGC GAA CTA TAA
Ala Leu Leu Ala Gly Arg Arg Arg Glu Leu Stop CHART B--pBG9

EcoRV
Sau3A           Rsa I           Taq I
GAT CTG ACC TAC GGT GTA CTG GCC GAT ATC GAA GCG GAA GAC

Dde I
CTG GCG CGT GAA GCG TCG TTT GCT CAG GGA TTA CGC GCG ATG

ATT GGC GGT ATC TTA ACC GCA TCC TGA TTC TCT CTC TTT TTC

GGC GGG CTG GTG ATA ACT GTG CCC GCG TTT CAT ATC GTA ATT

CHART B- -pBG9 -continued

```
                                              Eco RI
TCT CTG TGC AAA AAT TAT CCT TCC CGG CTT CGG AGA ATT CCC

Nde I
CCC AAA ATA TTC ACT GTA GCC ATA TGT CAT GAG AGT TTA TCG

Taq I
TTC CCA ATA CGC TCG AAC GAA CGT TCG GTT GCT TAT TTT ATG

Hinc II      Aha III              Sau3A
GCT TCT GTC AAC GCT GTT TTA AAG ATT AAT GCG ATC TAT ATC Sau3A
ACG CTG TGG GTA TTG CAG TTT TTG GTT TTT TGA TCG GGT GT . 10              Nco I     - - - - - - - - - - - - - -
CAG TTC TTT TTA TTT CCA TTT CTC TTC CAT GGG TTT CTC ACA Hinc II
- - - | - - - - - - - - - - - - - - - - -   Hpa I
GAT AAC TGT GTG CAA CAC AGA ATT GGT TAA CTA ATC AGA TTA Hinc II                      RBS          |
AAG GTT GAC CAG TAT TAT TAT CTT AAT GAG GAG TCC CTT ATG
                                                    Met Taq I
TTA CGT CCT GTA GAA ACC CCA ACC CGT GAA ATC AAA AAA CTC
Leu Arg Pro Val Glu Thr Pro Thr Arg Glu Ile Lys Lys Leu . Nru I
                       Sau3A
GAC GGC CTG TGG GCA TTC AGT CTG GAT CGC GAA AAC TGT GGA 87
Asp Gly Leu Trp Ala Phe Ser Leu Asp Arg Glu Asn Cys Gly Bcl I
     Sau3A
ATT GAT CAG CGT TGG TGG GAA AGC GCG TTA CAA GAA AGC CGG
Ile Asp Gln Arg Trp Trp Glu Ser Ala Leu Gln Glu Ser Arg GCA ATT GCT GTG CCA GGC AGT TTT AAC GAT CAG TTC GCC GAT
Ala Ile Ala Val Pro Gly Ser Phe Asn Asp Gln Phe Ala Asp GCA GAT ATT CGT AAT TAT GCG GGC AAC GTC TGG TAT CAG CGC 213
Ala Asp Ile Arg Asn Tyr Ala Gly Asn Val Trp Tyr Gln Arg Fnu4H
GAA GTC TTT ATA CCG AAA GGT TGG GCA GGC CAG CGT ATC GTG CTG
Glu Val Phe Ile Pro Lys Gly Trp Ala Gly Gln Arg Ile Val Leu
```

CHART B- -pBG9

```
         Taq I
CGT TTC GAT GCG GTC ACT CAT TAC GGC AAA GTG TGG GTC AAT
Arg Phe Asp Ala Val Thr His Tyr Gly Lys Val Trp Val Asn

Fnu4H
AAT CAG GAA GTG ATG GAG CAT CAG GGC GGC TAT ACG CCA TTT  345
Asn Gln Glu Val Met Glu His Gln Gly Gly Tyr Thr Pro Phe

Rsa I
GAA GCC GAT GTC ACG CCG TAT GTT ATT GCC GGG AAA AGT GTA
Glu Ala Asp Val Thr Pro Tyr Val Ile Ala Gly Lys Ser Val

CGT ATC ACC GTT TGT GTG AAC AAC GAA CTG AAC TGG CAG ACT
Arg Ile Thr Val Cys Val Asn Asn Glu Leu Asn Trp Gln Thr

ATC CCG CCG GGA ATG GTG ATT ACC GAC GAA AAC GGC AAG AAA  471
Ile Pro Pro Gly Met Val Ile Thr Asp Glu Asn Gly Lys Lys

Fusion site
                                         Taq I
                                           |
AAG CAG TCT TAC TTC CAT GAT TTC TTT AAC TCG ATG ACA TTA
Lys Gln Ser Tyr Phe His Asp Phe Phe Asn Ser Met Thr Leu Mst I
                     Fnu4H          Fnu4H
CTT ATA TCT GGT GGC GTA ACA CCT GCT GCA AAT GCT GCG CAA
Leu Ile Ser Gly Gly Val Thr Pro Ala Ala Asn Ala Ala Gln E
             |
CAC GAT GAA GCT CAA CAA AAT GCT TTT TAT CAA GTG TTA AAT  697
His Asp Glu Ala Gln Gln Asn Ala Phe Tyr Gln Val Leu Asn Bcl I
                 Sau3A
ATG CCT AAC TTA AAC GCT GAT CAA CGT AAT GGT TTT ATC CAA
Met Pro Asn Leu Asn Ala Asp Gln Arg Asn Gly Phe Ile Gln Sau3A
AGC CTT AAA GAT GAT CCA AGC CAA AGT GCT AAC GTT TTA GGT  681
Ser Leu Lys Asp Asp Pro Ser Gln Ser Ala Asn Val Leu Gly D
                                         |
GAA GCT CAA AAA CTT AAT GAC TCT CAA GCT CCA AAA GCT GAT
Glu Ala Gln Lys Leu Asn Asp Ser Gln Ala Pro Lys Ala Asp Mst I                        Sau3A        Hae II
GCG CAA CAA AAT AAG TTC AAC AAA GAT CAA CAA AGC GCC TTC
Ala Gln Gln Asn Lys Phe Asn Lys Asp Gln Gln Ser Ala Phe
```

CHART B- -pBG9

```
TAT GAA ATC TTG AAC ATG CCT AAC TTA AAC GAG GAG CAA CGC 807
Tyr Glu Ile Leu Asn Met Pro Asn Leu Asn Glu Glu Gln Arg

Sau3A
AAT GGT TTC ATT CAA AGT CTT AAA GAC GAT CCA AGC CAA AGC
Asn Gly Phe Ile Gln Ser Leu Lys Asp Asp Pro Ser Gln Ser

ACT AAC GTT TTA GGT GAA GCT AAA AAA TTA AAC GAA TCT CAA
Thr Asn Val Leu Gly Glu Ala Lys Lys Leu Asn Glu Ser Gln

A
          |
GCA CCG AAA GCT GAC AAC AAT TTC AAC AAA GAA CAA CAA AAT 933
Ala Pro Lys Ala Asp Asn Asn Phe Asn Lys Glu Gln Gln Asn

GCT TTC TAT GAA ATC TTG AAC ATG CCT AAC TTG AAC GAA GAA
Ala Phe Tyr Glu Ile Leu Asn Met Pro Asn Leu Asn Glu Glu

Hind III
CAA CGC AAT GGT TTC ATC CAA AGC TTA AAA GAT GAC CCA AGT 1017
Gln Arg Asn Gly Phe Ile Gln Ser Leu Lys Asp Asp Pro Ser CAA AGT GCT AAC CTT TTA GCA GAA GCT AAA AAG TTA AAT GAA
Gln Ser Ala Asn Leu Leu Ala Glu Ala Lys Lys Leu Asn Glu B
              |
TCT CAA GCA CCG AAA GCT GAT AAC AAA TTC AAC AAA GAA CAA
Ser Gln Ala Pro Lys Ala Asp Asn Lys Phe Asn Lys Glu Gln CAA AAT GCT TTC TAT GAA ATC TTA CAT TTA CCT AAC TTA AAT 1143
Gln Asn Ala Phe Tyr Glu Ile Leu His Leu Pro Asn Leu Asn Hind III
GAA GAA CAA CGC AAT GGT TTC ATC CAA AGC TTA AAA GAT GAC
Glu Glu Gln Arg Asn Gly Phe Ile Gln Ser Leu Lys Asp Asp Hae II
CCA AGC CAA AGC GCT AAC CTT TTA GCA GAA GCT AAA AAG CTA
Pro Ser Gln Ser Ala Asn Leu Leu Ala Glu Ala Lys Lys Leu C
                     |
AAT GAT GCA CAA GCA CCA AAA GCT GAC AAC AAA TTC AAC AAA 1269
Asn Asp Ala Gln Ala Pro Lys Ala Asp Asn Lys Phe Asn Lys GAA CAA CAA AAT GCT TTC TAT GAA ATT TTA CAT TTA CCT AAC
Glu Gln Gln Asn Ala Phe Tyr Glu Ile Leu His Leu Pro Asn TTA ACT GAA GAA CAA CGT AAC GGC TTC ATC CAA AGC CTT AAA
Leu Thr Glu Glu Gln Arg Asn Gly Phe Ile Gln Ser Leu Lys
```

-continued

CHART B- -pBG9

Sau3A
GAC GAT CCT TCA GTG AGC AAA GAA ATT TTA GCA GAA GCT AAA <sup>1395</sup>
Asp Asp Pro Ser Val Ser Lys Glu Ile Leu Ala Glu Ala Lys S1
                                |
AAG CTA AAC GAT GCT CAA GCA CCA AAA GAG GAA GAC AAC AAC
Lys Leu Asn Asp Ala Gln Ala Pro Lys Glu Glu Asp Asn Asn S2                               S3
         |                               |
AAG CCT GGT AAA GAA GAC GGC AAC AAA CCT GGT AAA GAA GAC
Lys Pro Gly Lys Glu Asp Gly Asn Lys Pro Gly Lys Glu Asp S4                               S5
                  |                               |
GGC AAC AAA CCT GGT AAA GAA GAC AAC AAA AAC CTT GGC AAA <sup>1521</sup>
Gly Asn Lys Pro Gly Lys Glu Asp Asn Lys Asn Leu Gly Lys S6
                              |
GAA GAC GGC AAC AAA CCT GGT AAA GAA GAC AAC AAA AAA CCT
Glu Asp Gly Asn Lys Pro Gly Lys Glu Asp Asn Lys Lys Pro S7                              S8
       |                              |
GGC AAA GAA GAT GGC AAC AAA CCT GGT AAA GAA GAC GGC AAC
Gly Lys Glu Asp Gly Asn Lys Pro Gly Lys Glu Asp Gly Asn S9                             S10
                |                              |
AAG CCT GGT AAA GAA GAT GGC AAC AAA CCT GGT AAA GAA GAT <sup>1647</sup>
Lys Pro Gly Lys Glu Asp Gly Asn Lys Pro Gly Lys Glu Asp S11
                 |
GGC AAC AAG CCT GGT AAA GAA GAT GGC AAC AAG CCT GGT AAA
Gly Asn Lys Pro Gly Lys Glu Asp Gly Asn Lys Pro Gly Lys Cla I
                          Taq I
GAA GAC GGC AAC GGA GTC ATC G|AT GAT AAG CTG TCA AAC ATG <sup>1731</sup>
Glu Asp Gly Asn Gly Val Ile A|sp Asp Lys Leu Ser Asn Met
                                    | pBR322 ⟶

EcoRI
AGA ATT CTT GAA GAC GAA AGG GCC TCG TGA
Arg Ile Leu Glu Asp Glu Arg Ala Ser ***

CHART C - - pBG3

EcoRV
Sau3A               Rsa I            Taq I
GAT CTG ACC TAC GGT GTA CTG GCC GAT ATC GAA GCG GAA GAC

CHART C -- pBG3

```
                    Dde I
CTG GCG CGT GAA GCG TCG TTT GCT CAG GGA TTA CGC GCG ATG

ATT GGC GGT ATC TTA ACC GCA TCC TGA TTC TCT CTC TTT TTC

GGC GGG CTG GTG ATA ACT GTG CCC GCG TTT CAT ATC GTA ATT

Eco RI
TCT CTG TGC AAA AAT TAT CCT TCC CGG CTT CGG AGA ATT CCC

Nde I
CCC AAA ATA TTC ACT GTA GCC ATA TGT CAT GAG AGT TTA TCG

Taq I
TTC CCA ATA CGC TCG AAC GAA CGT TCG GTT GCT TAT TTT ATG

Hinc II      Aha III         Sau3A
GCT TCT GTC AAC GCT GTT TTA AAG ATT AAT GCG ATC TAT ATC Sau3A
ACG CTG TGG GTA TTG CAG TTT TTG GTT TTT TGA TCG CGG TGT −10                  Nco I    - - - - - - - - - - - - -
CAG TTC TTT TTA TTT CCA TTT CTC TTC CAT GGG TTT CTC ACA Hinc II
- - - | - - - - - - - - - - - - - - - -   Hpa I
GAT AAC TGT GTG CAA CAC AGA ATT GGT TAA CTA ATC AGA TTA Hinc II                   RBS         1
AAG GTT GAC CAG TAT TAT TAT CTT AAT GAG GAG TCC CTT ATG
                                                    Met Taq I
TTA CGT CCT GTA GAA ACC CCA ACC CGT GAA ATC AAA AAA CTC
Leu Arg Pro Val Glu Thr Pro Thr Arg Glu Ile Lys Lys Leu E
        Mst I             |
GAC GGC CTT GCG CAA CAC GAT GAA GCT CAA CAA AAT GCT TTT 87
Asp Gly Leu Ala Gln His Asp Glu Ala Gln Gln Asn Ala Phe
        protein A Bcl I
                                      Sau3A
TAT CAA GTG TTA AAT ATG CCT AAC TTA AAC GCT GAT CAA CGT
Tyr Gln Val Leu Asn Met Pro Asn Leu Asn Ala Asp Gln Arg Sau3A
AAT GGT TTT ATC CAA AGC CTT AAA GAT GAT CCA AGC CAA AGT 171
Asn Gly Phe Ile Gln Ser Leu Lys Asp Asp Pro Ser Gln Ser
```

-continued

CHART C -- pBG3

```
GCT AAC GTT TTA GGT GAA GCT CAA AAA CTT AAT GAC TCT CAA
Ala Asn Val Leu Gly Glu Ala Gln Lys Leu Asn Asp Ser Gln

D
            |         Mst I                              Sau3A
GCT CCA AAA GCT GAT GCG CAA CAA AAT AAG TTC AAC AAA GAT
Ala Pro Lys Ala Asp Ala Gln Gln Asn Lys Phe Asn Lys Asp

Hae II
CAA CAA AGC GCC TTC TAT GAA ATC TTG AAC ATG CCT AAC TTA  297
Gln Gln Ser Ala Phe Tyr Glu Ile Leu Asn Met Pro Asn Leu

AAC GAG GAG CAA CGC AAT GGT TTC ATT CAA AGT CTT AAA GAC
Asn Glu Glu Gln Arg Asn Gly Phe Ile Gln Ser Leu Lys Asp

Sau3A
GAT CCA AGC CAA AGC ACT AAC GTT TTA GGT GAA GCT AAA AAA
Asp Pro Ser Gln Ser Thr Asn Val Leu Gly Glu Ala Lys Lys

A
              |
TTA AAC GAA TCT CAA GCA CCG AAA GCT GAC AAC AAT TTC AAC  423
Leu Asn Glu Ser Gln Ala Pro Lys Ala Asp Asn Asn Phe Asn

AAA GAA CAA CAA AAT GCT TTC TAT GAA ATC TTG AAC ATG CCT
Lys Glu Gln Gln Asn Ala Phe Tyr Glu Ile Leu Asn Met Pro

Hind III
AAC TTG AAC GAA GAA CAA CGC AAT GGT TTC ATC CAA AGC TTA
Asn Leu Asn Glu Glu Gln Arg Asn Gly Phe Ile Gln Ser Leu AAA GAT GAC CCA AGT CAA AGT GCT AAC CTT TTA GCA GAA GCT  549
Lys Asp Asp Pro Ser Gln Ser Ala Asn Leu Leu Ala Glu Ala B
              |
AAA AAG TTA AAT GAA TCT CAA GCA CCG AAA GCT GAT AAC AAA
Lys Lys Leu Asn Glu Ser Gln Ala Pro Lys Ala Asp Asn Lys TTC AAC AAA GAA CAA CAA AAT GCT TTC TAT GAA ATC TTA CAT  633
Phe Asn Lys Glu Gln Gln Asn Ala Phe Tyr Glu Ile Leu His Hind III
TTA CCT AAC TTA AAT GAA GAA CAA CGC AAT GGT TTC ATC CAA
Leu Pro Asn Leu Asn Glu Glu Gln Arg Asn Gly Phe Ile Gln Hae II
AGC TTA AAA GAT GAC CCA AGC CAA AGC GCT AAC CTT TTA GCA
Ser Leu Lys Asp Asp Pro Ser Gln Ser Ala Asn Leu Leu Ala C
                                        |
GAA GCT AAA AAG CTA AAT GAT GCA CAA GCA CCA AAA GCT GAC  759
Glu Ala Lys Lys Leu Asn Asp Ala Gln Ala Pro Lys Ala Asp
```

CHART C - - pBG3

AAC AAA TTC AAC AAA GAA CAA CAA AAT GCT TTC TAT GAA ATT
Asn Lys Phe Asn Lys Glu Gln Gln Asn Ala Phe Tyr Glu Ile

TTA CAT TTA CCT AAC TTA ACT GAA GAA CAA CGT AAC GGC TTC
Leu His Leu Pro Asn Leu Thr Glu Glu Gln Arg Asn Gly Phe

Sau3A
ATC CAA AGC CTT AAA GAC GAT CCT TCA GTG AGC AAA GAA ATT <sup>885</sup>
Ile Gln Ser Leu Lys Asp Asp Pro Ser Val Ser Lys Glu Ile TTA GCA GAA GCT AAA AAG CTA AAC GAT GCT CAA GCA CCA AAA
Leu Ala Glu Ala Lys Lys Leu Asn Asp Ala Gln Ala Pro Lys S1                              S2
|                               |
GAG GAA GAC AAC AAC AAG CCT GGT AAA GAA GAC GGC AAC AAA
Glu Glu Asp Asn Asn Lys Pro Gly Lys Glu Asp Gly Asn Lys S3                              S4
        |                               |
CCT GGT AAA GAA GAC GGC AAC AAA CCT GGT AAA GAA GAC AAC <sup>1011</sup>
Pro Gly Lys Glu Asp Gly Asn Lys Pro Gly Lys Glu Asp Asn S5                              S6
                |                               |
AAA AAC CTT GGC AAA GAA GAC GGC AAC AAA CCT GGT AAA GAA
Lys Asn Leu Gly Lys Glu Asp Gly Asn Lys Pro Gly Lys Glu S7
                        |
GAC AAC AAA AAA CCT GGC AAA GAA GAT GGC AAC AAA CCT GGT
Asp Asn Lys Lys Pro Gly Lys Glu Asp Gly Asn Lys Pro Gly S8                      S9
    |                       |
AAA GAA GAC GGC AAC AAG CCT GGT AAA GAA GAT GGC AAC AAA <sup>1137</sup>
Lys Glu Asp Gly Asn Lys Pro Gly Lys Glu Asp Gly Asn Lys S10                         S11
        |                           |
CCT GGT AAA GAA GAT GGC AAC AAG CCT GGT AAA GAA GAT GGC
Pro Gly Lys Glu Asp Gly Asn Lys Pro Gly Lys Glu Asp Gly Cla I
                                            Taq I
AAC AAG CCT GGT AAA GAA GAC GGC AAC GGA GTC ATC G|AT GAT <sup>1221</sup>
Asn Lys Pro Gly Lys Glu Asp Gly Asn Gly Val Ile A|sp Asp
                                                 |
                                                 | pBR322 →

EcoRI
AAG CTG TCA AAC ATG AGA ATT CTT GAA GAC GAA AGG GCC TCG
Lys Leu Ser Asn Met Arg Ile Leu Glu Asp Glu Arg Ala Ser

CHART C - - pBG3

-continued

TGA
***

CHART D--pBG3-2

```
                          EcoRV
Sau3A            Rsa I            Taq I
GAT CTG ACC TAC GGT GTA CTG GCC GAT ATC GAA GCG AAA GAC

Dde I
CTG GCG CGT GAA GCG TCG TTT GCT CAG GGA TTA CGC GCG ATG
ATT GGC GGT ATC TTA ACC GCA TCC TGA TTC TCT CTC TTT TTC
GGC GGG CTG GTG ATA ACT GTG CCC GCG TTT CAT ATC GTA ATT

Eco RI
TCT CTG TGC AAA AAT TAT CCT TCC CGG CTT CGG AGA ATT CCC

Nde I
CCC AAA ATA TTC ACT GTA GCC ATA TGT CAT GAG AGT TTA TCG

Taq I
TTC CCA ATA CGC TCG AAC GAA CGT TCG GTT GCT TAT TTT ATG

Hinc II     Aha III          Sau3A
GCT TCT GTC AAC GCT GTT TTA AAG ATT AAT GCG ATC TAT ATC Sau3A
ACG CTG TGG GTA TTG CAG TTT TTG GTT TTT TGA TCG CGG TGT
        −10              Nco I    -------------
CAG TTC TTT TTA TTT CCA TTT CTC TTC CAT GGG TTT CTC ACA Hinc II
---|---------------          Hpa I
GAT AAC TGT GTG CAA CAC AGA ATT GGT TAA CTA ATC AGA TTA Hinc II                RBS        1
AAG GTT GAC CAG TAT TAT TAT CTT AAT GAG GAG TCC CTT ATG
                                                    Met Taq I
TTA CGT CCT GTA GAA ACC CCA ACC CGT GAA ATC AAA AAA CTC
Leu Arg Pro Val Glu Thr Pro Thr Arg Glu Ile Lys Lys Leu E
         Mst I           |
GAC GGC CTT GCG CAA CAC GAT GAA GCT CAA CAA AAT GCT TTT  87
Asp Gly Leu Ala Gln His Asp Glu Ala Gln Gln Asn Ala Phe
        protein A Bcl I
                                      Sau3A
TAT CAA GTG TTA AAT ATG CCT AAC TTA AAC GCT GAT CAA CGT
Tyr Gln Val Leu Asn Met Pro Asn Leu Asn Ala Asp Gln Arg
```

CHART D--pBG3-2
-continued

```
                                    Sau3A
AAT GGT TTT ATC CAA AGC CTT AAA GAT GAT CCA AGC CAA AGT 171
Asn Gly Phe Ile Gln Ser Leu Lys Asp Asp Pro Ser Gln Ser

GCT AAC GTT TTA GGT GAA GCT CAA AAA CTT AAT GAC TCT CAA
Ala Asn Val Leu Gly Glu Ala Gln Lys Leu Asn Asp Ser Gln

D
        |       Mst I                            Sau3A
GCT CCA AAA GCT GAT GCG CAA CAA AAT AAG TTC AAC AAA GAT
Ala Pro Lys Ala Asp Ala Gln Gln Asn Lys Phe Asn Lys Asp

Hae II
CAA CAA AGC GCC TTC TAT GAA ATC TTG AAC ATG CCT AAC TTA 297
Gln Gln Ser Ala Phe Tyr Glu Ile Leu Asn Met Pro Asn Leu

AAC GAG GAG CAA CGC AAT GGT TTC ATT CAA AGT CTT AAA GAC
Asn Glu Glu Gln Arg Asn Gly Phe Ile Gln Ser Leu Lys Asp

Sau3A
GAT CCA AGC CAA AGC ACT AAC GTT TTA GGT GAA GCT AAA AAA
Asp Pro Ser Gln Ser Thr Asn Val Leu Gly Glu Ala Lys Lys

A
                        |
TTA AAC GAA TCT CAA GCA CCG AAA GCT GAC AAC AAT TTC AAC 423
Leu Asn Glu Ser Gln Ala Pro Lys Ala Asp Asn Asn Phe Asn

AAA GAA CAA CAA AAT GCT TTC TAT GAA ATC TTG AAC ATG CCT
Lys Glu Gln Gln Asn Ala Phe Tyr Glu Ile Leu Asn Met Pro

Hind III
AAC TTG AAC GAA GAA CAA CGC AAT GGT TTC ATC CAA AGC TTA
Asn Leu Asn Glu Glu Gln Arg Asn Gly Phe Ile Gln Ser Leu AAA GAT GAC CCA AGT CAA AGT GCT AAC CTT TTA GCA GAA GCT 549
Lys Asp Asp Pro Ser Gln Ser Ala Asn Leu Leu Ala Glu Ala B
                            |
AAA AAG TTA AAT GAA TCT CAA GCA CCG AAA GCT GAT AAC AAA
Lys Lys Leu Asn Glu Ser Gln Ala Pro Lys Ala Asp Asn Lys TTC AAC AAA GAA CAA CAA AAT GCT TTC TAT GAA ATC TTA CAT 633
Phe Asn Lys Glu Gln Gln Asn Ala Phe Tyr Glu Ile Leu His Hind III
TTA CCT AAC TTA AAT GAA GAA CAA CGC AAT GGT TTC ATC CAA
Leu Pro Asn Leu Asn Glu Glu Gln Arg Asn Gly Phe Ile Gln
```

CHART D--pBG3-2

Hae II

```
AGC TTA AAA GAT GAC CCA AGC CAA AGC GCT AAC CTT TTA GCA
Ser Leu Lys Asp Asp Pro Ser Gln Ser Ala Asn Leu Leu Ala

C
                                             |
GAA GCT AAA AAG CTA AAT GAT GCA CAA GCA CCA AAA GCT GAC 759
Glu Ala Lys Lys Leu Asn Asp Ala Gln Ala Pro Lys Ala Asp

AAC AAA TTC AAC AAA GAA CAA CAA AAT GCT TTC TAT GAA ATT
Asn Lys Phe Asn Lys Glu Gln Gln Asn Ala Phe Tyr Glu Ile

TTA CAT TTA CCT AAC TTA ACT GAA GAA CAA CGT AAC GGC TTC
Leu His Leu Pro Asn Leu Thr Glu Glu Gln Arg Asn Gly Phe

Sau3A
ATC CAA AGC CTT AAA GAC GAT CCT TCA GTG AGC AAA GAA ATT 885
Ile Gln Ser Leu Lys Asp Asp Pro Ser Val Ser Lys Glu Ile

TTA GCA GAA GCT AAA AAG CTA AAC GAT GCT CAA GCA CCA AAA
Leu Ala Glu Ala Lys Lys Leu Asn Asp Ala Gln Ala Pro Lys

S1                          S2
      |                           |
GAG GAA GAC AAC AAC AAG CCT GGT AAA GAA GAC GGC AAC AAA
Glu Glu Asp Asn Asn Lys Pro Gly Lys Glu Asp Gly Asn Lys

S3                           S4
           |                            |
CCT GGT AAA GAA GAC GGC AAC AAA CCT GGT AAA GAA GAC AAC 1011
Pro Gly Lys Glu Asp Gly Asn Lys Pro Gly Lys Glu Asp Asn

S5                              S6
                |                               |
AAA AAC CTT GGC AAA GAA GAC GGC AAC AAA CCT GGT AAA GAA
Lys Asn Leu Gly Lys Glu Asp Gly Asn Lys Pro Gly Lys Glu

S7
                    |
GAC AAC AAA AAA CCT GGC AAA GAA GAT GGC AAC AAA CCT GGT
Asp Asn Lys Lys Pro Gly Lys Glu Asp Gly Asn Lys Pro Gly

S8                       S9
      |                        |
AAA GAA GAC GGC AAC AAG CCT GGT AAA GAA GAT GGC AAC AAA 1137
Lys Glu Asp Gly Asn Lys Pro Gly Lys Glu Asp Gly Asn Lys

S10                          S11
           |                            |
CCT GGT AAA GAA GAT GGC AAC AAG CCT GGT AAA GAA GAT GGC
Pro Gly Lys Glu Asp Gly Asn Lys Pro Gly Lys Glu Asp Gly
```

CHART D--pBG3-2

-continued

```
                                                              | stop
AAC AAG CCT GGT AAA GAA GAC GGC AAC GGA GTC ATC GGG CGC
Asn Lys Pro Gly Lys Glu Asp Gly Asn Gly Val Ile Gly Arg linker                    |
GCT AGC TAG CTA GCG CGC CCG
Ala Ser *** Leu Ala Arg Pro
```

What is claimed is:

1. A hybrid protein having the following amino acid sequence:
Met Leu Arg Pro Val Glu Thr Pro Thr Arg Glu Ile Lys Lys Leu Asp Gly Leu Trp Ala Phe Ser Leu Asp Arg Glu Asn Cys Gly Ile Asp Gln Arg Trp Trp Glu Ser Ala Leu Gln Glu Ser Arg Ala Ile Ala Val Pro Gly Ser Phe Asn Asp Gln Phe Ala Asp Ala Asp Ile Arg Asn Tyr Als Gly Asn Val Trp Tyr Gln Arg Glu Val Phe Ile Pro Lys Gly Trp Ala Gly Gln Arg Ile Val Leu Arg Phe Asp Ala Val Thr His Tyr Gly Lys Val Trp Val Asn Asn Gln Glu Val Met Glu His Gln Gly Gly Tyr Thr Pro Phe Glu Ala Asp Val Thr Pro Tyr Val Ile Ala Gly Lys Ser Val Arg Ile Thr Val Cys Val Asn Asn Glu Leu Asn Trp Gln Thr Ile Pro Pro Gly Met Val Ile Thr Asp Glu Asn Gly Lys Lys Lys Gln Ser Tyr Phe His Asp Phe Phe Asn Ser Met Thr Leu Leu Ile Ser Gly Gly Val Thr Pro Ala Ala Asn Ala Ala Gln His Asp Glu Ala Gln Gln Asn Ala Phe Tyr Gln Val Leu Asn Met Pro Asn Leu Asn Ala Asp Gln Arg Asn Gly Phe Ile Gln Ser Leu Lys Asp Asp Pro Ser Gln Ser Ala Asn Val Leu Gly Glu Ala Gln Lys Leu Asn Asp Ser Gln Ala Pro Lys Ala Asp Ala Gln Gln Asn Lys Phe Asn Lys Asp Gln Gln Ser Ala Phe Tyr Glu Ile Leu Asn Met Pro Asn Leu Asn Glu Glu Gln Arg Asn Gly Phe Ile Gln Ser Leu Lys Asp Asp Pro Ser Gln Ser Thr Asn Val Leu Gly Glu Ala Lys Lys Leu Asn Glu Ser Gln Ala Pro Lys Ala Asp Asn Asn Phe Asn Lys Glu Gln Gln Asn Ala Phe Tyr Glu ILe Leu Asn Met Pro Asn Leu Asn Glu Glu Gln Arg Asn Gly Phe Ile Gln Ser Leu Lys Asp Asp Pro Ser Gln Ser Ala Asn Leu Leu Ala Glu Ala Lys Lys Leu Asn Glu Ser Gln Ala Pro Lys Ala Asp Asn Lys Phe Asn Lys Glu Gln Gln Asn Ala Phe Tyr Glu Ile Leu His Leu Pro Asn Leu Thr Glu Glu Gln Arg Asn Gly Phe Ile Gln Ser Leu Lys Asp Asp Pro Ser Val Ser Lys Glu Ile Leu Ala Glu Ala Lys Lys Leu Asn Asp Ala Gln Ala Pro Lys Glu Glu Asp Asn Asn Lys Pro Gly Lys Glu Asp Gly Asn Lys Pro Gly Lys Glu Asp Gly Asn Lys Pro Gly Lys Glu Asp Asn Lys Asn Leu Gly Lys Glu Asp Gly Asn Lys Pro Gly Lys Glu Asp Asn Lys Lys Pro Gly Lys Glu Asp Gly Asn Lys Pro Gly Lys Glu Asp Gly Asn Lys Pro Gly Lys Glu Asp Gly Asn Lys Pro Gly Lys Glu Asp Gly Asn Lys Pro Gly Lys Glu Asp Gly Asn Gly Val Ile Asp Asp Lys Leu Ser Asn Met Arg Ile Leu Glu Asp Glu Arg Ala Ser.

2. A hybrid protein having the following amino acid sequence:
Met Leu Arg Pro Val Glu Thr Pro Thr Arg Glu Ile Lys Lys Leu Asp Gly Leu Ala Gln His Asp Glu Ala Gln Gln Asn Ala Phe Tyr Gln Val Leu Asn Met Pro Asn Leu Asn Ala Asp Gln Arg Asn Gly Phe Ile Gln Ser Leu Lys Asp Asp Pro Ser Gln Ser Ala Asn Val Leu Gly Glu Ala Gln Lys Leu Asn Asp Ser Gln Ala Pro Lys Ala Asp Ala Gln Gln Asn Lys Phe Asn Lys Asp Gln Gln Ser Ala Phe Tyr Glu Ile Leu Asn Met Pro Asn Leu Asn Glu Glu Gln Arg Asn Gly Phe Ile Gln Ser Leu Lys Asp Asp Pro Ser Gln Ser Thr Asn Val Leu Gly Glu Ala Lys Lys Leu Asn Glu Ser Gln Ala Pro Lys Ala Asp Asn Asn Phe Asn Lys Glu Gln Gln Asn Ala Phe Tyr Glu Ile Leu Asn Met Pro Asn Leu Asn Glu Glu Gln Arg Asn Gly Phe Ile Gln Ser Leu Lys Asp Asp Pro Ser Gln Ser Ala Asn Leu Leu Ala Glu Ala Lys Lys Leu Asn Glu Ser Gln Ala Pro Lys Ala Asp Asn Lys Phe Asn Lys Glu Gln Gln Asn Ala Phe Tyr Glu Ile Leu His Leu Pro Asn Leu Asn Glu Glu Gln Arg Asn Gly Phe Ile Gln Ser Leu Lys Asp Asp Pro Ser Gln Ser Ala Asn Leu Leu Ala Glu Ala Lys Lys Leu Asn Asp Ala Gln Ala Pro Lys Ala Asp Asn Lys Phe Asn Lys Glu Gln Gln Asn Ala Phe Tyr Glu Ile Leu His Leu Pro Asn Leu Thr Glu Glu Gln Arg Asn Gly Phe Ile Gln Ser Leu Lys Asp Asp Pro Ser Val Ser Lys Glu Ile Leu Ala Glu Ala Lys Lys Leu Asn Asp Ala Gln Ala Pro Lys Glu Glu Asp Asn Asn Lys Pro Gly Lys Glu Asp Gly Asn Lys Pro Gly Lys Glu Asp Gly Asn Lys Pro Gly Lys Glu Asp Asn Lys Lys Pro Gly Lys Glu Asp Gly Asn Lys Pro Gly Lys Glu Asp Gly Asn Lys Pro Gly Lys Glu Asp Gly Asn Lys Pro Gly Lys Glu Asp Gly Asn Lys Pro Gly Lys Glu Asp Gly Asn Gly Val Ile Asp Asp Lys Leu Ser Asn Met Arg Ile Leu Glu Asp Glu Arg Ala Ser.

3. A hybrid protein having the following amino acid sequence:
Met Leu Arg Pro Val Glu Thr Pro Thr Arg Glu Ile Lys Lys Leu Asp Gly Leu Ala Gln His Asp Glu Ala Gln Gln Asn Ala Phe Tyr Gln Val Leu Asn Met Pro Asn Leu Asn Ala Asp Gln Arg Asn Gly Phe Ile Gln Ser Leu Lys Asp Asp Pro Ser Gln Ser Ala Asn Val Leu Gly Glu Ala Gln Lys Leu Asn Asp Ser Gln Ala Pro Lys Ala Asp Ala Gln Gln Asn Lys Phe Asn Lys Asp Gln Gln Ser Ala Phe Tyr Glu Ile Leu Asn Met Pro Asn Leu Asn Glu Glu Gln Arg Asn Gly Phe Ile Gln Ser Leu Lys Asp Asp Pro Ser Gln Ser Thr Asn Val Leu Gly Glu Ala Lys Lys Leu Asn Glu Ser Gln Ala Pro Lys Ala Asp Asn Asn Phe Asn Lys Glu Gln Gln Asn Ala Phe Tyr Glu Ile Leu Asn Met Pro Asn Leu Asn Glu Glu Gln Arg Asn Gly Phe Ile Gln Ser Leu Lys Asp Asp Pro Ser Gln Ser Ala Asn Leu Leu Ala Glu Ala Lys Lys Leu Asn Glu Ser Gln Ala Pro Lys Ala Asp Asn Lys Phe Asn Lys Glu Gln Gln Asn Ala Phe Tyr Glu Ile Leu His Leu Pro Asn Leu Asn Glu Glu Gln Arg Asn Gly Phe Ile Gln Ser Leu Lys Asp Asp Pro Ser Gln Ser Ala Asn Leu Leu Ala Glu Ala Lys Lys Leu Asn Asp Ala Gln Ala Pro Lys Ala Asp Asn Lys Phe
Asn Lys Glu Gln Gln Asn Ala Phe Tyr Glu Ile Leu His
Leu Pro Asn Leu Thr Glu Glu Gln Arg Asn Gly Phe
Ile Gln Ser Leu Lys Asp Asp Pro Ser Val Ser Lys Glu
Ile Leu Ala Glu Ala Lys Lys Leu Asn Asp Ala Gln Ala
Pro Lys Glu Asp Asn Asn Lys Pro Gly Lys Glu
Asp Gly Asn Lys Pro Gly Lys Glu Asp Gly Asn Lys
Pro Gly Lys Glu Asp Asn Lys Asn Leu Gly Lys Glu
Asp Gly Asn Lys Pro Gly Lys Glu Asp Asn Lys Lys
Pro Gly Lys Glu Asp Gly Asn Lys Pro Gly Lys Glu
Asp Gly Asn Lys Pro Gly Lys Glu Asp Gly Asn Lys
Pro Gly Lys Glu Asp Gly Asn Lys Pro Gly Lys Glu
Asp Gly Asn Lys Pro Gly Lys Glu Asp Gly Asn Gly
Val Ile Gly Arg Ala Ser.

\* \* \* \* \*

UNITED STATES PATENT AND TRADEMARK OFFICE
CERTIFICATE OF CORRECTION

PATENT NO. : 4,691,009
DATED : September 1, 1987
INVENTOR(S) : Palmer et. al.

It is certified that error appears in the above-indentified patent and that said Letters Patent is hereby corrected as shown below:

Columns 29, 31 and 33,     line 1: Delete "Chart C-pBG3" and insert therefor -- Chart C - pBG5--.

Signed and Sealed this

Twenty-sixth Day of September, 1995

Attest:

BRUCE LEHMAN

Attesting Officer     Commissioner of Patents and Trademarks